United States Patent

Lee et al.

Patent Number: 6,001,830
Date of Patent: Dec. 14, 1999

[54] HETEROCYCLIC COMPOUNDS

[75] Inventors: Sung Jai Lee, Clarks Summit, Pa.; Yoshitaka Konishi, Osaka, Japan; Orest Taras Macina, Pittsburgh, Pa.; Kigen Kondo, Osaka, Japan; Dingwei Tim Yu, Easton; Manton Rodgers Frierson, Scranton, both of Pa.; Masafumi Sugitani, Osaka, Japan

[73] Assignee: Ono Pharmaceutical Co., Ltd., Osaka, Japan

[21] Appl. No.: 09/189,843

[22] Filed: Nov. 12, 1998

Related U.S. Application Data

[62] Division of application No. 08/393,995, Feb. 24, 1995, Pat. No. 5,869,486.

[51] Int. Cl.$^6$ .......... A61K 31/50; A61K 31/505; C07D 487/04; C07D 495/04
[52] U.S. Cl. .......... 514/248; 544/236; 544/263; 544/278; 514/258
[58] Field of Search .......... 544/236; 514/248

[56] References Cited

U.S. PATENT DOCUMENTS 5,011,835  4/1991  Peet et al. .......... 514/212

*Primary Examiner*—Mukund J. Shah
*Assistant Examiner*—Ann M. Kessinger
*Attorney, Agent, or Firm*—Stevens, Davis, Miller & Mosher, L.L.P.

[57] ABSTRACT

The compounds of the formula:

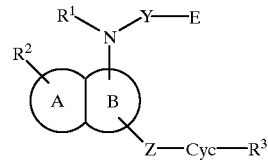

(I)

wherein ring

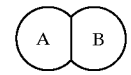

is a hetero ring containing nitrogen atom, optionally selected from

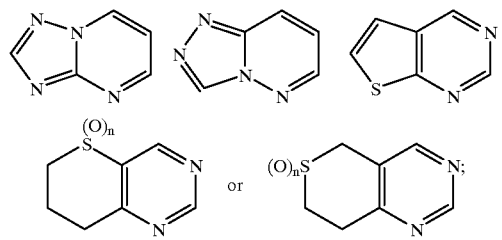

n is 0–2;
Y is bond or alkylene;
Z is bond, alkylene or vinylene;
E is
 (i) 4–15 membered, unsaturated, partially saturated or fully saturated, mono or bicyclic hetero ring containing as hetero atoms, 1 or 2 N atoms, 1 or 2 O atoms or 1 S atom,
 (ii) 4–15 membered, unsaturated or partially saturated, mono or bicyclic carbocyclic ring, or
 (iii) —OR$^4$ (in which R$^4$ is hydrogen atom, alkyl or alkyl substituted by a hydroxy group);
Cyc is 5–7 membered, unsaturated, partially saturated or fully saturated, monocyclic hetero ring containing as hetero atoms, 1 or 2 N atoms or 5–7 membered, unsaturated or partially saturated, monocyclic carbocyclic ring;
R$^1$ is H or alkyl;
R$^2$ is H, alkyl, alkoxy or halogen atom;
R$^3$ is H, alkyl, alkoxy or —COOR$^5$ (in which R$^5$ is H or alkyl);
with the proviso that
 (1) a Cyc ring should not bond to Z through a nitrogen atom in the Cyc ring when Z is vinylene and that
 (2) Y is not a single bond, when E is —OR$^4$;
or pharmaceutically acceptable acid addition salts thereof, pharmaceutically acceptable salts thereof, or hydrates thereof; have inhibitory effect on cGMP-PDE, or additionally on TXA$_2$ synthetase.

11 Claims, No Drawings

HETEROCYCLIC COMPOUNDS

This application is a divisional of U.S. patent application Ser. No. 08/393,995, filed Feb. 24, 1995 now U.S. Pat. No. 5,869,486.

FIELD OF THE INVENTION

The present invention relates to novel heterocyclic compounds. More particularly, this invention relates to:

(i) heterocyclic compounds of the following formula (I):

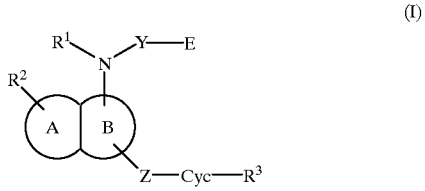

(I)

wherein all of the symbols have the same meanings as described hereinafter, and the pharmaceutically acceptable acid addition salts thereof, the pharmaceutically acceptable salts thereof, and the hydrates thereof, which have inhibitory activity on cyclic guanosine 3',5'-monophosphate phosphodiesterase, or additionally on thromboxane $A_2$ synthetase, (ii) processes for the preparation thereof, (iii) inhibitors of cyclic guanosine 3',5'-monophosphate phosphodiesterase, or additionally of thromboxane $A_2$ synthetase containing them, and (iv) methods of prevention and treatment of symptoms and diseases of mammals, including humans, by administering an effective amount of the compounds of the formula (I), the pharmaceutically acceptable acid addition salts thereof, the pharmaceutically acceptable salts thereof, and the hydrates thereof, to the patient to be treated.

1. Background of the Invention

Cyclic guanosine 3',5'-monophosphate (abbreviated as cGMP hereafter) was found in urine in rats by D. F. Ashman in 1963. Till now, it has been known that cGMP is distributed broadly in tissues of many animals including human beings. cGMP is biosynthesized from guanosine triphosphate (GTP) by the action of guanylate cyclase.

cGMP has been experimentally confirmed to have various physiological activities. For example, cGMP induces the relaxation of heart muscle and of smooth muscle. Further, it is related to the formation of neuronal synapses, and it acts as a trigger of cell proliferation and it induces the proliferation of lymphocyte.

cGMP is metabolized to physiologically inactive 5'-GMP by the action of cGMP phosphodiesterase (abbreviated as cGMP-PDE hereafter).

Accordingly, the inhibition of the action of cGMP-PDE is considered to be useful for the prevention and/or treatment of diseases induced by enhancement of the metabolism of cGMP, such as hypertension, heart failure, myocardial infarction, angina, atherosclerosis, cardiac edema, renal insufficiency, nephrotic edema, hepatic edema, asthma, bronchitis, dementia, immunodeficiency, pulmonary hypertension.

On the other hand, thromboxane $A_2$ (abbreviated as $TXA_2$ hereafter) was found as a constituent of the arachidonate cascade, in platelets by M. Hamberg in 1975. $TXA_2$ is biosynthesized from arachidonic acid released from cell membrane via prostaglandin $G_2$ and prostaglandin $H_2$, and rapidly metabolized to inactive thromboxane $B_2$. $TXA_2$ is known to induce platelet aggregation and to contract smooth muscle, particularly blood vessel muscle and bronchial muscle. $TXA_2$ synthetase was isolated and purified from microsome in platelets.

Accordingly, the inhibition of $TXA_2$ synthetase decreases the biosynthesis of $TXA_2$, and is useful for the prevention and/or treatment of inflammation, hypertension, thrombosis, arteriosclerosis, cerebral apoplexy, asthma, myocardial infarction, cardiostenosis, cerebral infarction, etc.

2. Related Arts

Up to now, some compounds have been known as cGMP-PDE inhibitors, for example,

Zaprinast

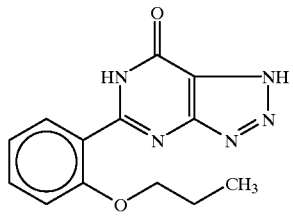

(A)

AR-L 57

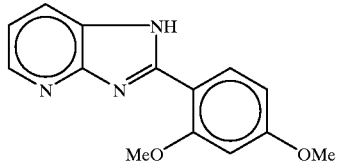

(B)

MY-5445

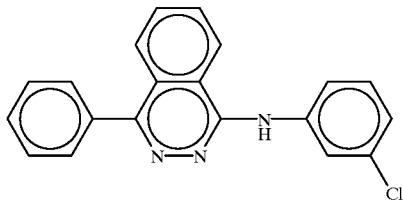

(C)

Many compounds derived from the above lead compounds have been proposed and many patent applications relating to those have been filed. For example, as derivatives of Zaprinast, compounds wherein the 1H-1,2,3-triazole skeleton is replaced by various other hetero cycles (see U.S. Pat. No. 5,047,404), those wherein the triazole is replaced by a benzene ring (see EP-371731), and those wherein the triazole is eliminated, i.e. those having only the pyrimidine skeleton (see EP-395328), have been proposed. The above mentioned compounds always contain an oxo group at the 4th position of the pyrimidine skeleton. The compounds having an amino group at the said position are described in U.S. Pat. No. 4,060,615. The specification discloses 4-amino-6,7-dimethoxy-2-piperazinylquinazoline derivatives of the following formula:

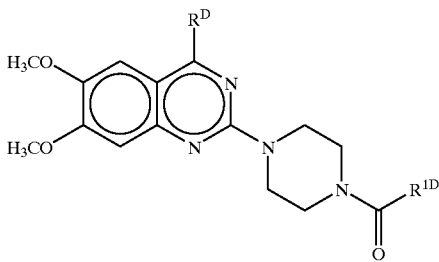

(D)

wherein $R^D$ is amino or hydrazino,
$R^{1D}$ is C3–8 cycloalkyl, C3–8 methylcycloalkyl or C4–8 cycloalkenyl, and their acid addition salts.

Recently, quinazoline derivatives having inhibitory activity on cGMP-PDE have been published (see WO 93/07124). In this specification, the quinazoline derivatives of the following formula is disclosed.

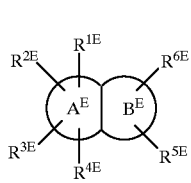

(E)

wherein ring $A^E$ is benzene, pyridine or cyclohexane ring;
ring $B^E$ is pyridine, pyrimidine or imidazole ring;
$R^{1E}$, $R^{2E}$, $R^{3E}$ and $R^{4E}$ are each, for example, hydrogen, halogen, lower alkyl optionally substituted by halogen, lower alkoxy, hydroxyalkyl, nitro, cyano, acylamino, optionally protected COOH, $S(O)n^E$—$R^{7E}$ ($n^E$ is 0,1,2, $R^{7E}$ is lower alkyl), $NR^{45E}R^{46E}$ ($R^{45E}$ and $R^{46E}$ are each, for example, hydrogen, lower alkyl);
$R^{5E}$ is, for example, optionally substituted heteroaryl (for example, pyridinyl, imidazolidinyl, qunazolidinyl);
$R^{6E}$ is, for example,

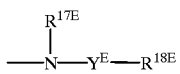

(1)

($R^{17E}$ is, for example, hydrogen, lower alkyl, alkoxyalkyl, hydroxyalkyl;
$Y^E$ is, for example, $(CH_2)q^E$ ($q^E$ is 0 to 8); $R^{18E}$ is, for example, hydrogen, hydroxy, optionally substituted heteroaryl, optionally substituted cycloalkyl),

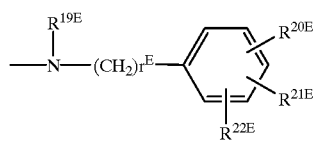

(2)

($R^{19E}$ is, for example, hydrogen, lower alkyl; $R^{20E}$, $R^{21E}$ and $R^{22E}$ are each, for example, hydrogen, halogen, nitro, low alkyl, alkoxy; $r^E$ is 0 to 8);
and a pharmacologinically acceptable salt thereof.

More recently, nitrogenous fused-heterocyclic derivatives having inhibitory activity on cGMP-PDE have been published (see WO 94/22855). In this specification, the nitrogenous fused-heterocyclic derivatives of the following formula is disclosed.

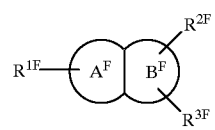

(F)

wherein ring $A^F$ is benzene, pyridine or cyclohexane ring;
ring $B^F$ is pyridine, imidazole or pyrimidine ring;
$R^{1F}$ is —$NR^{4F}R^{5F}$ (wherein $R^{4F}$ and $R^{5F}$ are each, independently, hydrogen atom, lower alkyl acyl group or a carbonyl group which may be protected, or alternatively $R^{4F}$ and $R^{5F}$ may form a ring together with the nitrogen atom to which they are bonded, provided that the ring may bus substituted) or heteroaryl group which has one or two nitrogen atoms and may be substituted;
$R^{2F}$ is hydrogen atom, a group represented by the formula

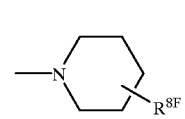

(1)

(wherein $R^{8F}$ is a carboxyl or tetrazolyl group which may be protected), or a halogen atom;
$R^{3F}$ is a hydrogen atom or a group represented by the formula

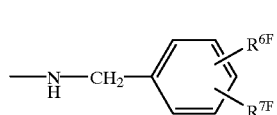

(2)

(wherein $R^{6F}$ and $R^{7F}$ are each, independently, hydrogen or halogen atom or a lower alkyl group, or alternatively $R^{6F}$ and $R^{7F}$ may together form a methylenedioxy or ethylenedioxy group);
and a pharmacologinically acceptable salt thereof.

Furthermore, some $TXA_2$ synthetase inhibitors have been known, for example,

OKY-046

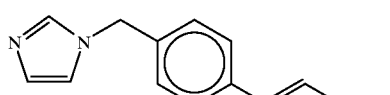

(G)

ONO-1581

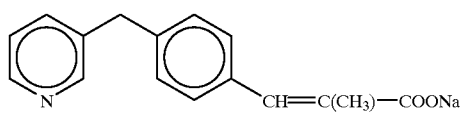

(H)

Many derivatives containing an imidazole or pyridine ring as the basic skeleton have been proposed.

Recently, quinazoline derivatives have inhibitory effect on cGMP-PDE, or additionally on $TXA_2$ synthetase have been published (see EP-579496). In this specification, the quinazoline derivatives of the following formula is disclosed.

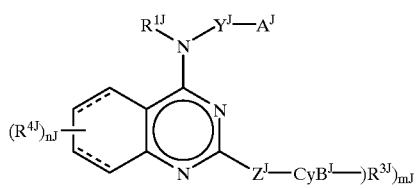

(J)

wherein $R^{1J}$ is hydrogen or C1–4 alkyl;
$Y^J$ is single bond or C1–6 alkylene;
$A^J$ is
(i) —$CyA^J$—$(R^{2J})l^J$,
(ii) —O—$R^{QJ}$ or —S(O)$p^J$—$R^{QJ}$ or
(iii) —$NR^{16J}R^{17J}$;
in which $R^{QJ}$ is hydrogen, C1–4 alkyl, hydroxy-C1–4 alkyl or —$CyA^J$—$(R^{2J})l^J$;
$R^{16J}$ and $R^{17J}$ independently are hydrogen or C1–4 alkyl;
$p^J$ is 0–2;
$CyA^J$ is
(1) carbocyclic mono-ring of 3–7 membered, saturated or unsaturated,
(2) heterocyclic mono-ring of 4–7 membered containing one nitrogen, unsaturated or partially saturated,
(3) heterocyclic mono-ring of 4–7 membered containing one nitrogen and one oxygen, unsaturated or partially saturated,
(4) heterocyclic mono-ring of 4–7 membered containing one nitrogen and two oxygens, unsaturated or partially saturated,
(5) heterocyclic mono-ring of 4–7 membered containing two nitrogen and one oxygen, unsaturated or partially saturated,
(6) heterocyclic mono-ring of 4–7 membered containing one or two sulfur, unsaturated or partially saturated or
(7) heterocyclic mono-ring of 4–7 membered containing one or two oxygen, unsaturated, fully or partially saturated or saturated;
$R^{2J}$ is (1) hydrogen, (2) C1–4 alkyl, (3) C1–4 alkoxy, (4) —$COOR^{5J}$, in which $R^{5J}$ is hydrogen or C1–4 alkyl,
(5) —$NR^{6J}R^{7J}$, in which $R^{6J}$ and $R^{7J}$ independently are hydrogen or C1–4 alkyl, (6) —$SO_2NR^{6J}R^{7J}$, in which $R^{6J}$ and $R^{7J}$ are as hereinbefore defined, (7) halogen,
(8) trifluoromethyl, (9) nitro or (10) trifluoromethoxy;
$Z^J$ is single bond, methylene, ethylene, vinylene or ethynylene;
$CyB^J$ is
(1) heterocyclic mono-ring of 4–7 membered containing one nitrogen, unsaturated or partially saturated,
(2) heterocyclic mono-ring of 4–7 membered containing two nitrogen, unsaturated or partially saturated,
(3) heterocyclic mono-ring of 4–7 membered containing three nitrogen, unsaturated or partially saturated,
(4) heterocyclic mono-ring of 4–7 membered containing ore or two oxygen, unsaturated or partially saturated, or
(5) heterocyclic mono-ring of 4–7 membered containing one or two sulfur, unsaturated or partially saturated;
$R^{3J}$ is hydrogen, C1–4 alkyl, C1–4 alkoxy, halogen or trifluoromethyl;

$R^{4J}$ is (1) hydrogen, (2) C1–4 alkyl, (3) C1–4 alkoxy, (4) —$COOR^{8J}$, in which $R^{8J}$ is hydrogen or C1–4 alkyl,
(5) —$NR^{9J}R^{10J}$, in which $R^{9J}$ is hydrogen, C1–4 alkyl or phenyl(C1–4 alkyl) and $R^{10J}$ is hydrogen or C1–4 alkyl, (6) —$NHCOR^{11J}$, in which $R^{11J}$ is C1–4 alkyl,
(7) —$NHSO_2R^{11J}$, in which $R^{11J}$ is as hereinbefore defined, (8) $SO_2NR^{9J}R^{10J}$, in which $R^{9J}$ and $R^{10J}$ are as hereinbefore defined, (9) —$OCOR^{11J}$, in which $R^{11J}$ is as hereinbefore defined, (10) halogen, (11) trifluoromethyl, (12) hydroxy, (13) nitro, (14) cyano, (15) —$SO2N$=$CHNR^{12J}R^{13J}$ in which $R^{12J}$ is hydrogen or C1–4 alkyl and $R^{13J}$ is C1–4 alkyl, (16) —$CONR^{14J}R^{15J}$ in which $R^{14J}$ is hydrogen or C1–4 alkyl or phenyl(C1–4 alkyl) and $R^{15J}$ is C1–4 alkyl or
(17) C1–4alkylthio, (18) C1–4 alkylsulfinyl, (19) C1–4 alkylsulfonyl, (20) ethynyl, (21) hydroxymethyl, (22) tri(C1–4alkyl)silyl or (23) acetyl;
and $l^J$, $m^J$ and $n^J$ independently are 1 or 2;
with the proviso that
(1) the group of the formula: —$CyA^J$—$(R^{2J})_l^J$ does not represent a cyclopentyl and trifluoromethylphenyl group when $Y^J$ is a single bond, that
(2) a $CyB^J$ ring should not bond to $Z^J$ through a nitrogen atom in the $CyB^J$ ring when $Z^J$ is vinylene or ethynylene, that
(3) a $CyB^J$ ring should not pyridine or thiophene when $CyA^J$ is a ring of $CyA^J$-(7) and that
(4) $Y^J$ is not a single bond, when $A^J$ is (ii) —O—$R^{QJ}$ or —S(O)$p^J$—$R^{QJ}$ or (iii) —$NR^{16J}R^{17J}$;
or pharmaceutically acceptable acid addition salts thereof, pharmaceutically acceptable salts thereof, or hydrates thereof.

Thienopyrimidine derivatives have plant protection agents and against fungi viruses, bacteria and insects have been published (see USP-4146716). In this specification, the thienopyrimidine derivatives of the following formula is disclosed.

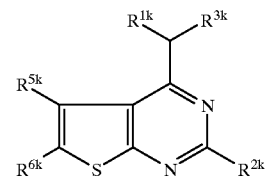

(K)

wherein $R^{1k}$ and $R^{3k}$ are H, $NH_2$, alkyl, alkenyl, alkynyl, cycloalkyl, aralkyl, aryl or acyl, optionally substituted; —$NR^{1k}R^{3k}$ forms a heterocyclic ring; $R^{2k}$ is H halogen atom, OH, SH, CN, $NH_2$, —$NHNH_2$, alkyl, alkoxy, alkenyl, alkynyl, cycloalkyl, aralkyl, aryl, alkylthio optionally substituted by alkanesuphonyl or alkanesulphinyl, carboxylic acid, ester or amide group or heterocyclic group; $R^{5k}$ and $R^{6k}$ are H, halogen atom, $NO_2$, halosulphonyl, CN, alkyl, alkenyl, alkynyl, cycloalkyl, aralkyl, aryl, acyl, alkylamino, aroyl, $NH_2$, acloxy, amidosulphonyl, alkylthio, optionally substituted by alkanesuphonyl, carboxylic acid, ester or amide group or $R^{5k}$ and $R^{6k}$ forms ring.

Thiopyranopyrimidine derivatives have hypoglycemic activity have been published (see Chem. Pharm. Bull., 34, 4150(1986)).

Each of the foregoing documents are herein incorporated, in their entirety, by reference.

PURPOSE OF THE INVENTION

Energetic investigation has been carried out in order to discover compounds having inhibitory activities on cGMP- PDE or additionally TXA₂synthetase, and as a result, the present inventors have found the compounds of the present invention.

SUMMARY OF THE INVENTION

The present invention relates to:
(i) heterocyclic compounds of the formula (I):

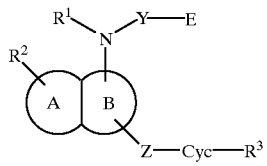

wherein ring

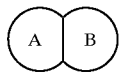

is a hetero ring containing nitrogen atom, selected from

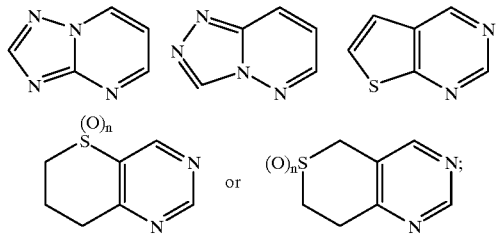

n is 0–2;
Y is single bond or C1–6 alkylene;
Z is single bond, C1–2 alkylene or vinylene;
E is
  (i) 4–15 membered, unsaturated, partially saturated or fully saturated, mono or bicyclic hetero ring containing as hetero atoms, one or two nitrogen atoms, one or two oxygen atoms or one sulfur atom,
  (ii) 4–15 membered, unsaturated or partially saturated, mono or bicyclic carbocyclic ring, or
  (iii) —OR⁴ (in which R⁴ is hydrogen atom, C1–4 alkyl or C1–4 alkyl substituted by a hydroxy group);
Cyc is 5–7 membered, unsaturated, partially saturated or fully saturated, monocyclic hetero ring containing as hetero atoms, one or two nitrogen atoms or 5–7 membered, unsaturated or partially saturated, monocyclic carbocyclic ring;
R¹ is hydrogen atom or C1–4 alkyl;
R² is hydrogen atom, C1–4 alkyl, C1–4alkoxy or halogen atom;
R³ is hydrogen atom, C1–4 alkyl, C1–4alkoxy or —COOR⁵ (in which R⁵ is hydrogen atom or C1–4 alkyl);
with the proviso that
  (1) a Cyc ring should not bond to Z through a nitrogen atom in the Cyc ring when Z is vinylene and that
  (2) Y is not a single bond, when E is —OR⁴;
or pharmaceutically acceptable acid addition salts thereof, pharmaceutically acceptable salts thereof, or hydrates thereof, (ii) process for the preparation thereof,
(iii) cGMP-PDE inhibitors, or additionally TXA₂synthetase inhibitors, containing them as active ingredient, and
(iv) methods of prevention and treatment of mammals, including humans, by administering an effective amount of the compounds of the formula (I), the pharmaceutically acceptable acid addition salts thereof, the pharmaceutically acceptable salts thereof, and the hydrates thereof, to the patient to be treated.

COMPARISON

There is no description of the compounds of the formula (I) of the present invention in those of the formulae (E), (F) and (J) mentioned above. The compounds of the formula (I) of the present invention have the following ring of the formula:

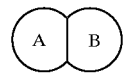

(wherein

is a hetero ring containing nitrogen atom, selected from)

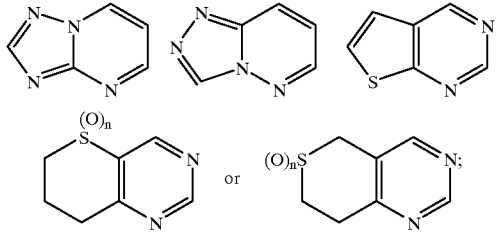

in their structure.

On the other hand, the basic skelton of the compounds of the formula (E) in the related arts are the following ring of the formula:

(wherein ring A^E is benzene, pyridine or cyclohexane ring; ring B^E is pyridine, pyrimidine or imidazole ring) group.

And the basic skelton of the compounds of formula (F) in the related arts are the following ring of the formula:

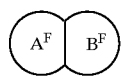

(wherein ring $A^F$ is benzene, pyridine or cyclohexane ring; ring $B^F$ is pyridine, pyrimidine or imidazole ring).

Further, the compounds of formula (J) in the related arts are merely a basic skelton of quinazoline.

Ring structures of the compounds in the related arts are different from the ring of the compounds of the present invention, i.e., kinds, number of the hetero atoms contained in them and/or ring-number of the rings are different from each other.

Accordingly, the compounds of the present invention are quite novel.

Furthermore, the fact that compounds of the present invention have inhibitory activity on cGMP-PDE or additionally $TXA_2$ synthetase, is not suggested from pharmaceutical use disclosed in related arts of (E) and (F) mentioned above. Accordingly, the compounds of the present invention are useful for the prevention and/or treatment of diseases induced by only enhancement of the metabolism of cGMP, or the increase of $TXA_2$, or induced by both factors.

DETAILED DESCRIPTION OF THE INVENTION

In the formula (I), the C1–4 alkyl group represented by $R^1$, $R^2$, $R^3$, $R^4$ in E and $R^5$ mean methyl, ethyl, propyl, butyl and the isomers thereof.

In the formula (I), the C1–4 alkoxy group represented by $R^2$ and $R^3$ mean methoxy, ethoxy, propoxy, butoxy and isomers thereof.

In the formula (I), the halogen atom represented by $R^2$ mean fluorine, chlorine, bromine and iodine.

In the formula (I), the C1–6 alkylene group represented by Y means methylene, ethylene, trimethylene, tetramethylene, pentamethylene, hexamethylene and isomers thereof.

In the formula (I), the C1–2 alkylene group represented by Z means methylene, ethylene and isomers thereof.

In the formula (I), the C1–4 alkyl substituted by a hydroxy group represented by $R^4$ in E means methyl, ethyl, propyl, butyl and the isomers thereof, which are substituted by a hydroxy group.

In the formula (I), 5–7 membered, unsaturated, partially saturated or fully saturated, monocyclic hetero ring containing as hetero atoms, one or two nitrogen atoms represented by Cyc includes pyrrole, pyrroline, pyrrolidine, imidazole, imidazoline, imidazolidine, pyrazole, pyrazoline, pyrazolidine, pyridine, piperidine, pyridazine, pyrimidine, pyrazine, piperazine and azepine etc.

In the formula (I), 5–7 membered, unsaturated or partially saturated, monocyclic carbocyclic ring represented by Cyc includes cyclopentadiene, cyclopentene, benzene, cyclohexadiene, cyclohexene, cycloheptatriene, cycloheptadiene and cycloheptaene etc.

In the formula (I), 4–15 membered, unsaturated, partially saturated or fully saturated, mono or bicyclic hetero ring containing as hetero atoms, one or two nitrogen atoms, one or two oxygen atoms or one sulfur atom represented by E includes furan, pyran, dioxole, dioxine, benzofuran, benzopyran, benzodioxole, benzodioxine, thiophene, thioine (thiopyran), benzothiophene, benzothione (benzothiopyran), thiazole, isothiazole, thiazine, benzothiazole, benzoisothiazole, benzothiazine and partially or fully saturated ring thereof.

In the formula (I), 4–15 membered, unsaturated or partially saturated, mono or bicyclic carbocyclic ring represented by E includes cyclopentadiene, benzene, cycloheptatriene, indene, naphthalene and partially saturated ring thereof.

Preferred compounds of the present invention are listed as follows:

heterocyclic compounds of the formula I (1)

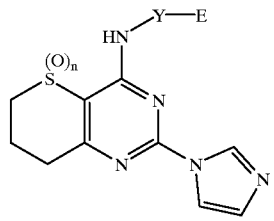

wherein Y, E and n are the same meaning as hereinbefore defined, respectively, the formula I (2)

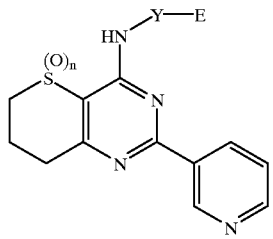

wherein Y, E and n are the same meaning as hereinbefore defined, respectively, the formula I (3)

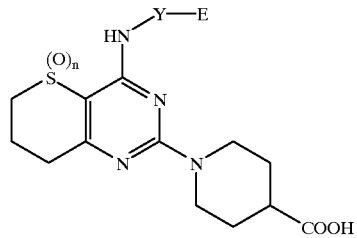

wherein Y, E and n are the same meaning as hereinbefore defined, respectively, the formula I (4)

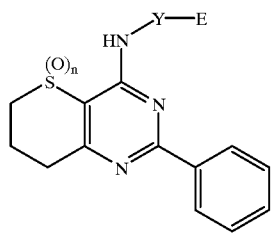

I(4)

wherein Y, E and n are the same meaning as hereinbefore defined, respectively, the formula I (5)

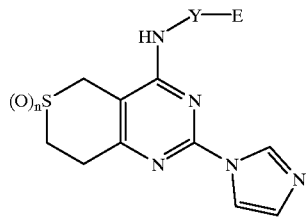

I(5)

wherein Y, E and n are the same meaning as hereinbefore defined, respectively, the formula I (6)

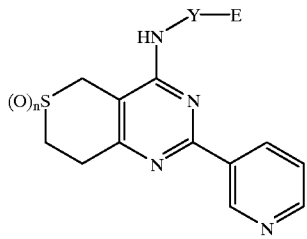

I(6)

wherein Y, E and n are the same meaning as hereinbefore defined, respectively, the formula I (7)

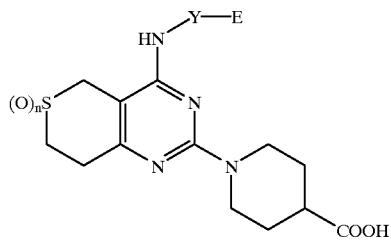

I(7)

wherein Y, E and n are the same meaning as hereinbefore defined, respectively, the formula I (8)

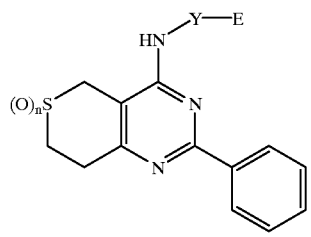

I(8)

wherein Y, E and n are the same meaning as hereinbefore defined, respectively, the formula I (9)

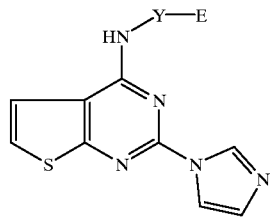

I(9)

wherein Y, E and n are the same meaning as hereinbefore defined, respectively, the formula I (10)

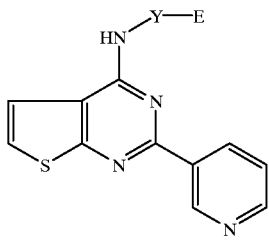

I(10)

wherein Y, E and n are the same meaning as hereinbefore defined, respectively, the formula I (11)

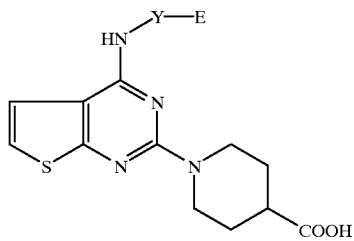

I(11)

wherein Y, E and n are the same meaning as hereinbefore defined, respectively, the formula I (12)

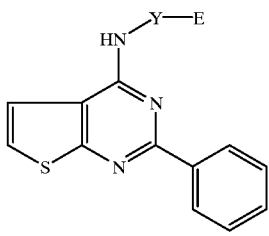

wherein Y, E and n are the same meaning as hereinbefore defined, respectively, the formula I (13)

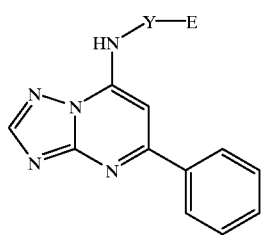

wherein Y, E and n are the same meaning as hereinbefore defined, respectively, the formula I (14)

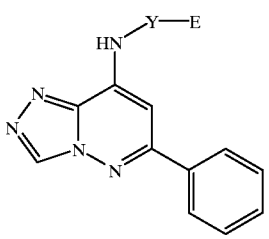

wherein Y, E and n are the same meaning as hereinbefore defined, respectively, pharmaceutically acceptable acid addition salts thereof, pharmaceutically acceptable salts thereof and hydrates thereof, Examples of representative compounds of the present invention are listed as follows:

TABLE 1

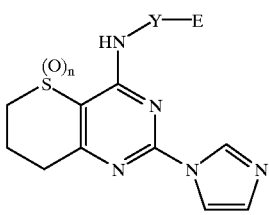

(IA)

(IB)

TABLE 2

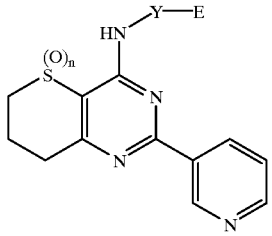

(IC)

| No. | | n | Y | E |
|---|---|---|---|---|
| 1 | (IA) or (IB) | 0 | methylene | 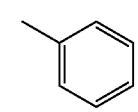 |
| 2 | (IA) or (IB) | 0 | methylene | 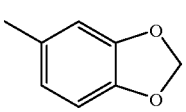 |
| 3 | (IA) or (IB) | 0 | ethylene | 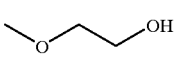 |
| 4 | (IA) or (IB) | 1 | methylene | 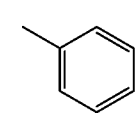 |
| 5 | (IA) or (IB) | 1 | methylene | 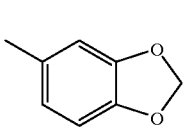 |
| 6 | (IA) or (IB) | 1 | ethylene | 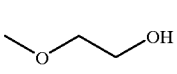 |
| 7 | (IA) or (IB) | 2 | methylene | 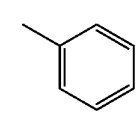 |
| 8 | (IA) or (IB) | 2 | methylene | 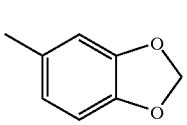 |
| 9 | (IA) or (IB) | 2 | ethylene |  |

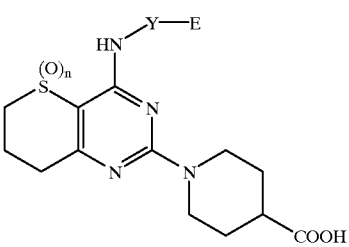

(ID)

15

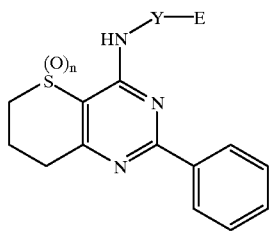

| No. | | n | Y | E |
|---|---|---|---|---|
| 1 | (IC) or (ID) | 0 | methylene | phenyl |
| 2 | (IC) or (ID) | 0 | methylene | benzo[1,3]dioxole |
| 3 | (IC) or (ID) | 0 | ethylene | methoxyethanol |
| 4 | (IC) or (ID) | 1 | methylene | phenyl |
| 5 | (IC) or (ID) | 1 | methylene | benzo[1,3]dioxole |
| 6 | (IC) or (ID) | 1 | ethylene | methoxyethanol |
| 7 | (IC) or (ID) | 2 | methylene | phenyl |
| 8 | (IC) or (ID) | 2 | methylene | benzo[1,3]dioxole |
| 9 | (IC) or (ID) | 2 | ethylene | methoxyethanol |

16

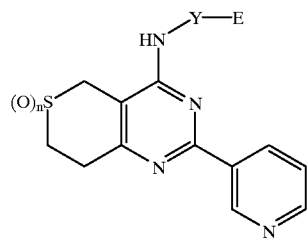

| No. | | n | Y | E |
|---|---|---|---|---|
| 1 | (IE) or (IF) | 0 | methylene | phenyl |
| 2 | (IE) or (IF) | 0 | methylene | benzo[1,3]dioxole |
| 3 | (IE) or (IF) | 0 | ethylene | methoxyethanol |
| 4 | (IE) or (IF) | 1 | methylene | phenyl |
| 5 | (IE) or (IF) | 1 | methylene | benzo[1,3]dioxole |
| 6 | (IE) or (IF) | 1 | ethylene | methoxyethanol |
| 7 | (IE) or (IF) | 2 | methylene | phenyl |
| 8 | (IE) or (IF) | 2 | methylene | benzo[1,3]dioxole |
| 9 | (IE) or (IF) | 2 | ethylene | methoxyethanol |

TABLE 3

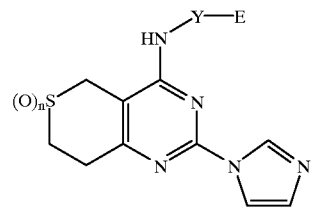

(IE)

(IF)

TABLE 4

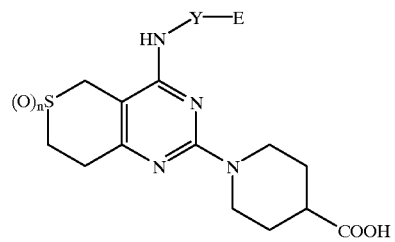

(IG)

(IH)

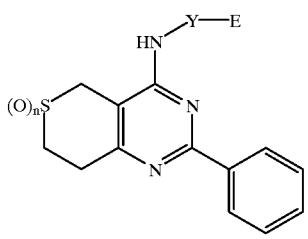

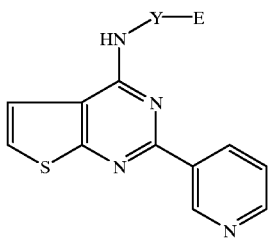

| No. | | n | Y | E |
|---|---|---|---|---|
| 1 | (IG) or (IH) | 0 | methylene | phenyl |
| 2 | (IG) or (IH) | 0 | methylene | methylenedioxyphenyl |
| 3 | (IG) or (IH) | 0 | ethylene | methoxyethanol |
| 4 | (IG) or (IH) | 1 | methylene | phenyl |
| 5 | (IG) or (IH) | 1 | methylene | methylenedioxyphenyl |
| 6 | (IG) or (IH) | 1 | ethylene | methoxyethanol |
| 7 | (IG) or (IH) | 2 | methylene | phenyl |
| 8 | (IG) or (IH) | 2 | methylene | methylenedioxyphenyl |
| 9 | (IG) or (IH) | 2 | ethylene | methoxyethanol |

| No. | | Y | E |
|---|---|---|---|
| 1 | (IJ) or (IK) | methylene | phenyl |
| 2 | (IJ) or (IK) | methylene | methylenedioxyphenyl |
| 3 | (IJ) or (IK) | ethylene | methoxyethanol |

TABLE 5

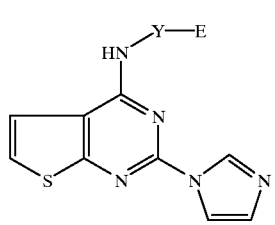

(IJ)

(IK)

TABLE 6

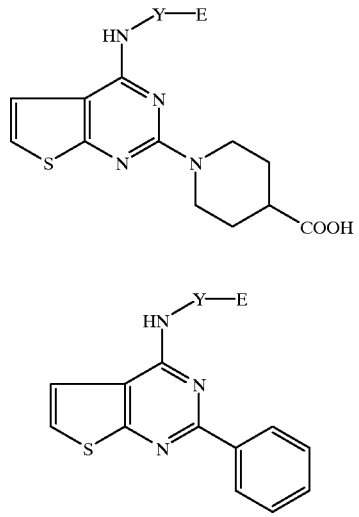

(IL)

(IM)

| No. | | Y | E |
|---|---|---|---|
| 1 | (IL) or (IM) | methylene | phenyl |
| 2 | (IL) or (IM) | methylene | methylenedioxyphenyl |
| 3 | (IL) or (IM) | ethylene | methoxyethanol |

TABLE 7

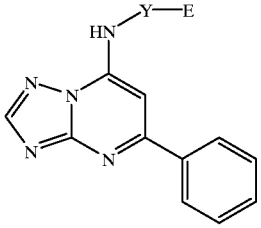
(IN)

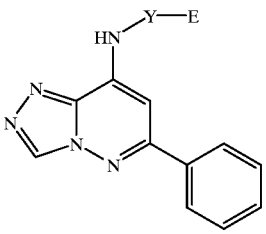
(IO)

| No. | | Y | E |
|---|---|---|---|
| 1 | (IN) or (IO) | methylene | 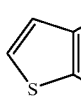 |
| 2 | (IN) or (IO) | methylene | 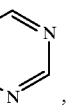 |
| 3 | (IN) or (IO) | ethylene | 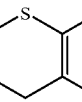 |
| 4 | (IN) or (IO) | methylene | 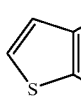 | and further those described in Examples below are also representative compounds of the present invention.

Salts and Acid Addition Salts

The compounds of the formula (I), if desired, may be converted into acid addition salts by known methods. Preferably, acid addition salts are non-toxic and water-soluble. The suitable acid addition salts are, for example, salts of an inorganic acid such as hydrochloric acid, hydrobromic acid, hydroiodic acid, sulfuric acid, phosphoric acid, nitric acid, or an organic acid such as acetic acid, lactic acid, tartaric acid, benzoic acid, citric acid, methanesulfonic acid, ethanesulfonic acid, benzenesulfonic acid, toluenesulfonic acid, isethionic acid, glucuronic acid and gluconic acid.

The compounds of the formula (I), if desired, may be converted into salts by known methods. Preferable, salts are non-toxic salts and water-soluble. The suitable salts are salts of alkaline metal (sodium, potassium etc.), salts of alkaline earth metal (calcium, magnesium etc.), ammonium salts, salts of pharmaceutically acceptable organic amine (tetramethylammonium, triethylamine, methylamine, dimethylamine, cyclopentylamine, phenylmethylamine, phenethylamine, piperidine, monoethanolamine, diethanolamine, tris(hydroxymethyl)methylamine, lysine, arginine, N-methyl-D-glucamine etc.).

Throughout the specification including claims, it may be easily understood by those skilled in the art, that the alkyl, alkoxy, groups include straight-chained and also branched-chained ones. Accordingly, all isomers produced by the difference in stereo configuration, such as asymmetric carbons are included in the present invention.

Process for the Preparation

In the compounds of the formula (I), of the present invention, the compound of the formula (I-1)

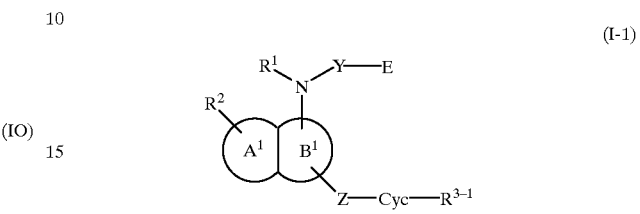
(I-1)

wherein

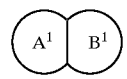

is selected from

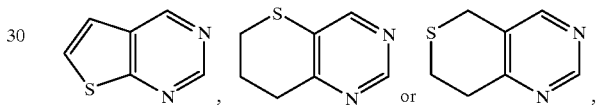

$R^{3-1}$ do not represent COOH group, and the other symbols are the same meaning as hereinbefore defined may be prepared by method (a) to (c) as follow.

(a) In the formula (I-1), of the present invention, those in which Z is the same meaning as hereinbefore defined and Z is bonded directly to a carbon atom in the ring represented by Cyc, i.e., the compound of the formula (I-a)

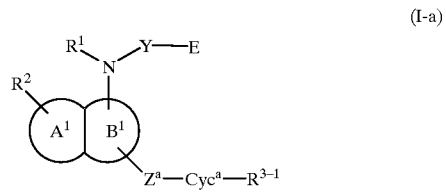
(I-a)

wherein $Z^a$ is the same meaning as hereinbefore defined for Z, $Cyc^a$ is the same meaning as hereinbefore defined for Cyc, provided that $Z^a$ is bonded directly to a carbon atom in the ring represented by $Cyc^a$, and the other symbols are as hereinbefore defined may be prepared by reacting a compound of the formula (II-a)

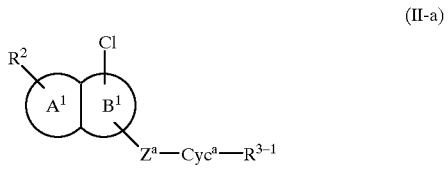
(II-a)

wherein all the symbols are the same meaning as hereinbefore defined with an amine of the formula (III)

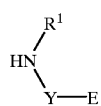

(III)

wherein all the symbols are the same meaning as hereinbefore defined.

This reaction may be carried out, for example, in a proper organic solvent such as a lower alkanol (e.g. ethanol) or tetrahydrofuran, or a mixture thereof, at a temperature from ambient to reflux, for several hours to several days, if necessary in the presence of a base such as triethylamine.

(b) In the formula (I-1), of the present invention, those in which Z represents single bond or methylene and Z is bonded directly to a nitrogen atom in the hetero ring represented by Cyc, i.e., the compound of the formula (I-b)

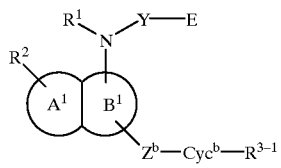

(I-b)

wherein $Z^b$ is single bond or methylene, $Cyc^b$ is the same meaning as hereinbefore defined for Cyc, provided that $Z^b$ is bonded directly to a nitrogen atom in the ring represented by $Cyc^b$, and the other symbols are as hereinbefore defined may be prepared by reacting a compound of the formula (II-a)

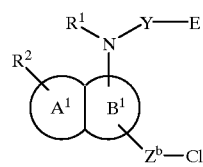

(II-b)

wherein all the symbols are the same meaning as hereinbefore defined with a heterocyclic amine of the formula (IV)

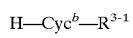   (IV)

H—$Cyc^b$—$R^{3-1}$ wherein all the symbols are the same meaning as hereinbefore defined.

This reaction may be carried out, for example, in a suitable organic solvent, such as alcohol (e.g., phenol or isopropyl alcohol) at a reflux temperature for several hours.

(c) In the formula (I-1), of the present invention, those in which Z represents ethylene and Z is bonded directly to a nitrogen atom in the hetero ring represented by Cyc, i.e., the compound of the formula (I-c)

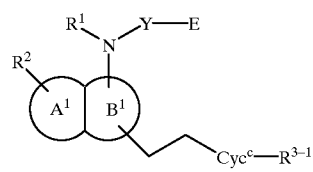

(I-c)

wherein $Cyc^c$ is the same meaning as hereinbefore defined for Cyc, provided that ethylene is bonded directly to a nitrogen atom in the ring represented by $Cyc^c$, and the other symbols are the same meaning as hereinbefore defined may be prepared by reacting a compound of the formula (II-c)

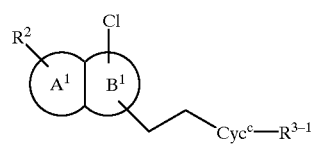

(II-c)

wherein all the symbols are the same meaning as hereinbefore defined with an amine of the formula (III).

This reaction may be carried out by the same method as hereinbefore described.

In the compounds of the formula (I), of the present invention, the compound of the formula (I-2)

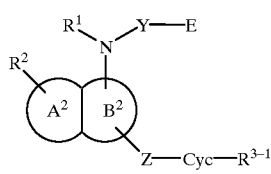

(I-2)

wherein

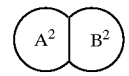

is selected from

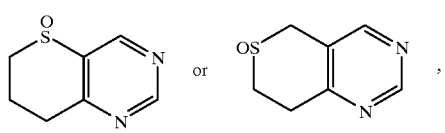

and the other symbols are the same meaning as hereinbefore defined may be prepared by oxidation of a corresponding compound having sulfide group, prepared, for example, by a method as hereinbefore described, i.e., of a compound of the formula (I-d)

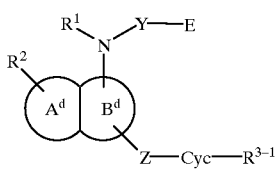
(I-d)

wherein

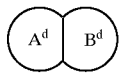

is selected from

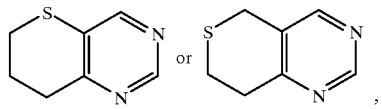

and the other symbols are the same meaning as hereinbefore defined.

This reaction may be carried out, for example, in a suitable organic solvent (e.g., dichloromethane, chloroform, benzene, hexane or t-butyl alcohol) in the presence of 1 equivalent of oxidation reagent (e.g., hydrogen peroxide, sodium periodate, acyl nitrites, sodium perborate or peracid (for example 3-chloroperoxybenzoic acid, peracetic acid)), at a temperature from −40° C. to 0° C. for several minutes.

In the compounds of the formula (I), of the present invention, the compound of the formula (I-3)

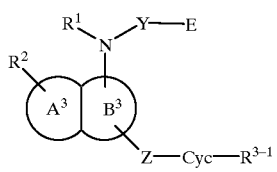
(I-3)

wherein

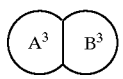

is selected from

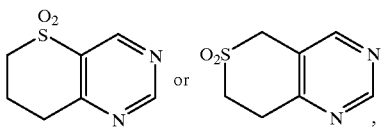

and the other symbols are the same meaning as hereinbefore defined may be prepared by oxidation of a corresponding compound having sulfide group of the formula (I-d).

This reaction may be carried out, for example, in a proper organic solvent (e.g., dichloromethane, chloroform, benzene, hexane or t-butyl alcohol) in the presence of excess of oxidation reagent (e.g., hydrogen peroxide, sodium periodate, potassium permanganate, sodium perborate, potassium hydrogen persulfate or peracid (for example 3-chloroperoxybenzoic acid, peracetic acid)), at a temperature from 0° C. to 40° C. for several hours.

In the compounds of the formula (I), of the present invention, the compound of the formula (I-4)

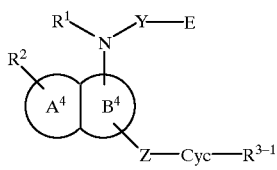
(I-4)

wherein

is selected from

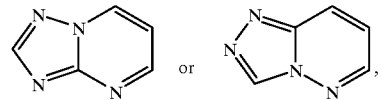

and the other symbols are the same meaning as hereinbefore defined may be prepared by reacting a compound of the formula (II-e)

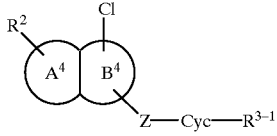
(II-e)

wherein all the symbols are the same meaning as hereinbefore defined with an amine of the formula (III).

This reaction may be carried out by the same method as hereinbefore described.

In the compounds of the formula (I), of the present invention, the compound of the formula (I-5)

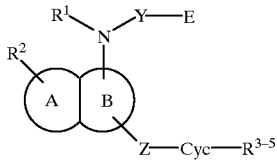
(I-5)

wherein $R^{3-5}$ represents COOH group, and the other symbols are the same meaning as hereinbefore defined may be prepared by hydrolysis of a compound of the formula (I-1), (I-2), (I-3) or (I-4) having ester group, i.e., a compound of the formula (I-f)

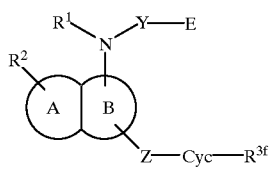

(I-f)

wherein $R^{3f}$ represents $COOR^{5f}$ (in which $R^{5f}$ represents C1–4 alkyl), and the other symbols are the same meaning as hereinbefore defined.

Hydrolysis of an ester bond is known per se, for example, under alkaline or acid conditions. Hydrolysis in alkaline conditions may be carried out, for example, in an appropriate organic solvent (e.g., methanol), using a hydroxide or a carbonate of alkali metals or alkaline earth metals, at a temperature of from 0° C. to 40° C. Hydrolysis in acid conditions may be carried out, for example, in an appropriate organic solvent (e.g., dichloromethane, chloroform, methanol, dioxane, ethyl acetate, anisole), or a mixture of them, in presence of an organic acid (e.g., trifluoroacetic acid), or inorganic acid (e.g., hydrochloric acid, sulfuric acid), or a mixture of them, at a temperature of from 0° C. to 90° C.

The compounds of the formulae (II-a), (II-b), (II-c) or (II-e) may be prepared by using known reactions. For example, they may be prepared by application or adaptation of the methods of Scheme 1 to 4 or methods described in the Example.

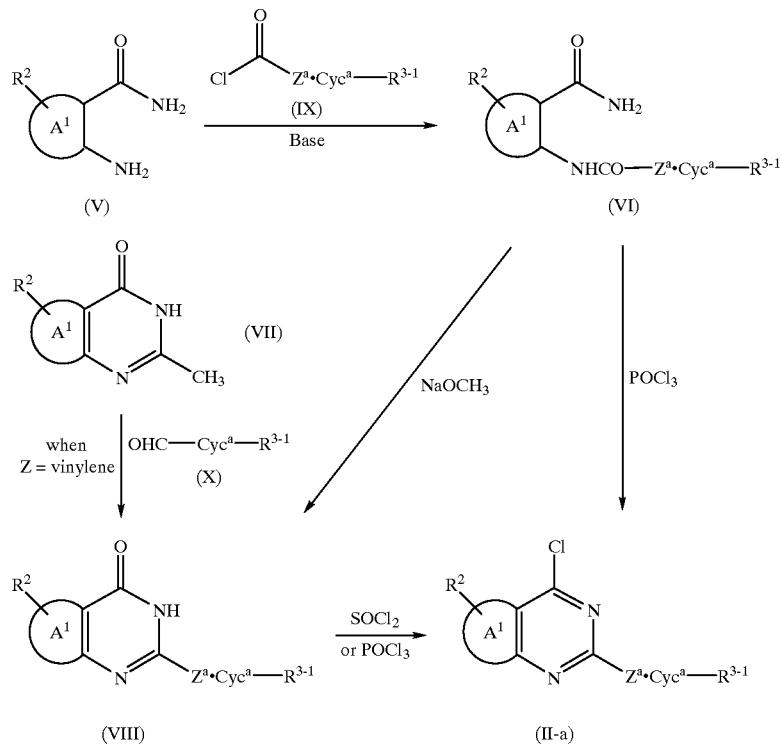

Scheme 1

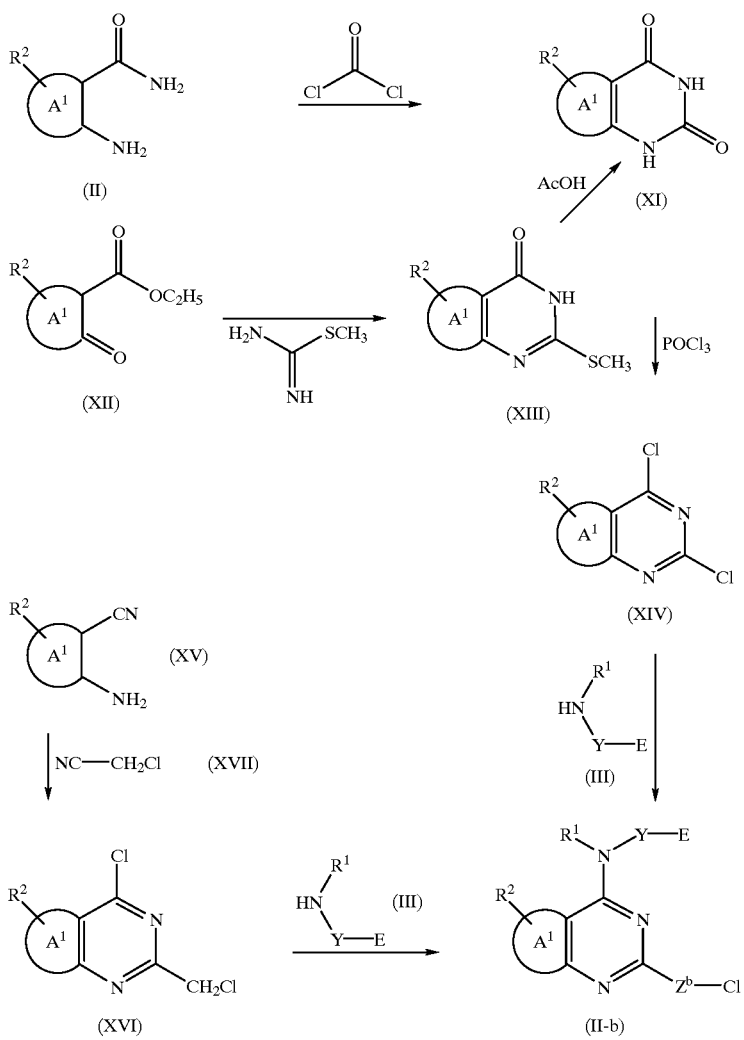
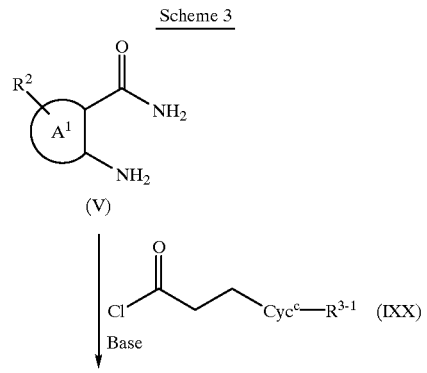
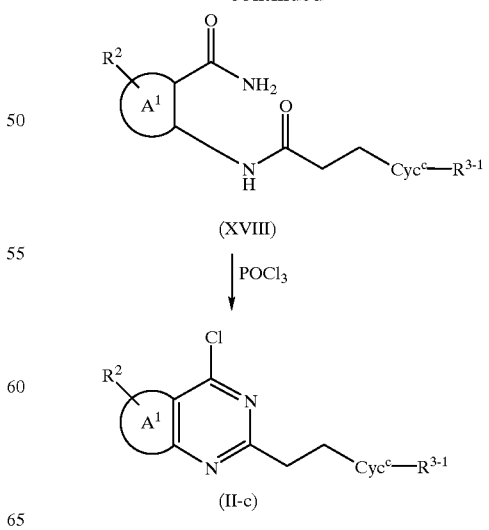

Scheme 4

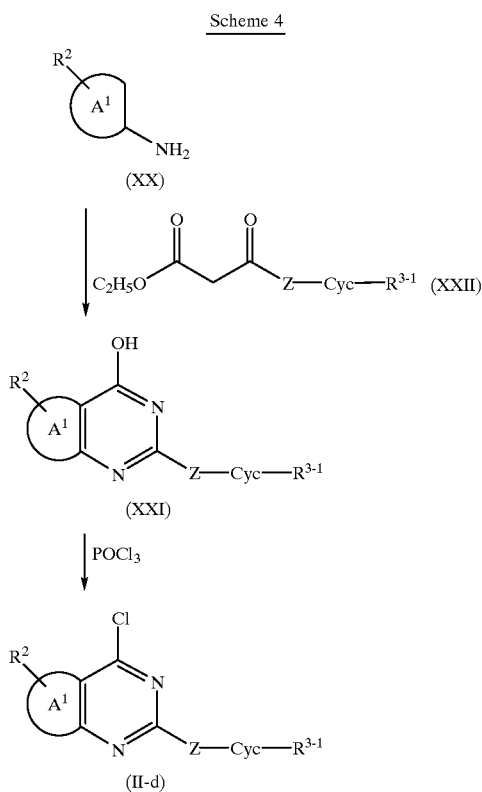

Each reaction in Scheme 1 to 4 may be carried out by methods known per se, under conditions described therein.

In each reaction in the present specification, products may be purified by conventional manner. For example, purification may be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

The starting materials and each reagent used in the process for the preparation of the present invention are known per se or may be easily prepared by known methods.

Effect

The compounds of the formula (I), pharmaceutically acceptable acid addition salts thereof, pharmaceutically acceptable salts thereof, or hydrates thereof, of the present invention have an inhibitory effect on cGMP-PDE, or additionally on $TXA_2$ synthetase, and are, therefore, useful for the prevention and/or treatment of not only diseases induced by enhancement of the metabolism of cGMP, such as hypertension, heart failure, myocardial infarction, angina, atherosclerosis, cardiac edema, renal insufficiency, nephrotic edema, hepatic edema, asthma, bronchitis, dementia, immunodeficiency, pulmonary hypertension, but also diseases induced by enhancement of the synthesis of $TXA_2$ such as inflammation, thrombosis, cerebral apoplexy, asthma, cardiostenosis, cerebral infarction etc, in mammals, especially in humans.

The inhibitory effect on cGMP-PDE and $TXA_2$ synthetase, of the compounds of the present invention were confirmed by screening tests as described below.

(1) Inhibitory Effect on cGMP-PDE

Method

PDE IC was isolated from human platelets according to standard methods previously described in Lugnier, C. et al., *Biochem. Pharmacol.* 35: 1743, 1986(incorporated in its entirety by reference). Typically, connective tissue and adventitia were removed and 1–2 units of platelets were suspended in 10 volumes of buffer A (20 mM Tris-HCl, pH 7.5, containing 2 mM magnesium acetate, 1 mM dithiothreitol, and 5 mM Na2EDTA) using a Brinkman polytron. The proteinase inhibitors leupeptin, pepstatin A, and phenylmethyl-sulfonyl fluoride (PMSF) were also included in this buffer (final concentration of 100 nM each). The homogenate was centrifuged at 100,000 g for 60 minutes. The supernatant was then removed and filtered through four layers of cheesecloth. The supernatant was applied to a DWAE-Trisacryl M column. The column was washed with several bed volumes of buffer B (20 mM Tris-HCl, pH 7.5, containing 2 mM magnesium acetate, 1 mM dithiothreitol, and proteinase inhibitors) and eluted by two successive linear NaCl gradients (0.05–0.15 M, 300 ml total, 0.15–0.40 M, 200 ml total). Five milliliter fractions were collected and assayed for cyclic GMP PDE activity.

Phosphodiesterase activity was measured, as described by Thompson, et al., *Adv. Cyclic Nucleotide Res.* 10:69, 1979 (incorporated in its entirety by reference), in a reaction medium containing 40 mM Tris-HCl (pH 8.0), 5 mM $MgCl_2$, and 1 mM dithiothreitol. The concentration of substrate ($^3$H-cGMP) was 0.2 mM. Compounds of the present invention were dissolved in dimethyl sulfoxide (DMSO) at a final concentration of 2.5%. This concentration of DMSO inhibited enzyme activity by approximately 10%. The $IC_{50}$ values (concentration that produced 50% inhibition of substrate hydrolysis) for the compounds examined were determined from concentration-response curves in which concentrations typically ranged from $10^{-8}$ to $10^{-3}$ M for the less potent inhibitors (half-log increments).

Result

TABLE 8

| Inhibitory activity on cGMP-PDE | | |
|---|---|---|
| Compounds Example No. | | Inhibitory activity $IC_{50}$ (M) |
| 2 | (2HCl salt) | $1.25 \times 10^{-7}$ |
| 2(3) | (2HCl salt) | $1.0 \times 10^{-7}$ |
| 2(5) | ($CH_3SO_3H$ salt) | $1.0 \times 10^{-7}$ |
| 2(7) | ($CH_3SO_3H$ salt) | $2.4 \times 10^{-8}$ |
| 4 | (free base) | $3.8 \times 10^{-7}$ |
| 5 | ($CH_3SO_3H$ salt) | $3.2 \times 10^{-6}$ |
| 6(1) | ($CH_3SO_3H$ salt) | $3.8 \times 10^{-7}$ |
| 7 | (free base) | $3.1 \times 10^{-6}$ |
| 8 | (free base) | $9.4 \times 10^{-7}$ |

(2) Inhibitory Effect on $TXA_2$ Synthetase

Method

Male Wistar rats were starved overnight. Five hundreds microliter of heparinized (10 U/mL) whole blood was collected from abdominal aorta using polyethylene syringe (needle: 22 or 26 G). The blood freshly drawn from animal was preincubated with 5 μL of test compound at 37° C. Five minutes later, 2.5 μL of 6 mM of Ca ionophore A23187 (final concentration of 30 μM) was added into tube, and incubation mixture was further incubated for 15 min. The reaction was terminated by centrifugation of tubes at 12,000 rpm for 2 min. $TXB_2$ content in the supernatant was determined by EIA as follows.

One milliliter of 0.5 M glycine-HCl buffer (pH 3.2) was added to 100 μL of sample. The samples were mixed well and centrifuged at 1,700 G for 10 min at 4° C. The extracted supernatant was applied to a SEP-PAK (registered Trade Mark) $C_{18}$ cartridge (Waters Assoc.). After washing with 10 mL of distilled water followed by 10 mL each of 15% ethanol and petroleum ether, the sample was eluted with 3 mL of ethyl acetate. The ethyl acetate fraction was evaporated to dryness under gentle $N_2$ stream and the residue was dissolved in EIA buffer (final volume of 1 mL) following the addition of 300 μL of 0.01M $NaHCO_3$-NaOH buffer (pH 10.0). EIA for $TXB_2$ was carried out according to a legend attached to the kit (Chyman Chemical Co., Inc.). Overall recovery of $TXB_2$ in this extraction procedure was 90%. The $IC_{50}$ values (concentration that produced 50% inhibition of $TXB_2$ synthesis) for the compounds examined were determined from concentration-response curves.

Result

TABLE 9

Inhibitory activity on $TXA_2$ synthetase

| Compounds Example No. | | Inhibitory activity (%) |
|---|---|---|
| 2(7) | ($CH_3SO_3H$ salt) | 63% at 10 μM |

On the other hand, it was confirmed that the acute toxicity of the compound of the present invention is very weak. Therefore, the compounds of the present invention may be considered to be sufficiently safe and suitable for pharmaceutical use.

Application for Pharmaceuticals

For the purpose above described, the compounds, of the formula (I), of the present invention, pharmaceutically acceptable acid addition salts thereof and hydrates thereof may be normally administered systemically or partially, usually by oral or parenteral administration.

The doses to be administered are determined depending upon age, body weight, symptom, the desired therapeutic effect, the route of administration, and the duration of the treatment etc. In the human adult, the doses per person are generally between 1 mg and 1000 mg, by oral administration, up to several times per day, and between 1 mg and 100 mg, by parenteral administration up to several times per day, or continuous administration between 1 and 24 hours per day intravenously.

As mentioned above, the doses to be used depend upon various conditions. Therefore, there are cases in which doses lower than or greater than the ranges specified above may be used.

Administration of the compounds of the present invention, may be as solid compositions, liquid compositions or other compositions for oral administration, as injections, liniments or suppositories etc. for parenteral administration.

Solid compositions for oral administration include compressed tablets, pills, capsules, dispersible powders, and granules. Capsules include hard capsules and soft capsules.

In such compositions, one or more of the active compound(s) is or are, admixed with at least one inert diluent (such as lactose, mannitol, glucose, hydroxypropyl cellulose, micro crystalline cellulose, starch, polyvinylpyrrolidone, magnesium metasilicate aluminate etc.) The compositions may also comprise, as is normal practice, additional substances other than inert diluents: e.g. lubricating agents (such as magnesium stearate etc.), disintegrating agents (such as cellulose calcium glycolate etc.), stabilizing agents (such as lactose etc.), and assisting agents for dissolving (such as glutamic acid, aspartic acid etc.).

The tablets or pills may, if desired, be coated with film of gastric or enteric material (such as sugar, gelatin, hydroxypropyl cellulose or hydroxypropylmethyl cellulose phthalate etc.), or be coated with more than two films. And further, coating may include containment within capsules of absorbable materials such as gelatin.

Liquid compositions for oral administration include pharmaceutically-acceptable solutions, emulsions, suspensions, syrups and elixirs.

In such compositions, one or more of the active compound(s) is or are comprise in inert diluent(s) commonly used in the art (purified water, ethanol etc.).

Besides inert diluents, such compositions may also comprise adjuvants (such as wetting agents, suspending agents etc.), sweetening agents, flavoring agents, perfuming agents and preserving agents.

Other compositions for oral administration include spray compositions which may be prepared by known methods and which comprise one or more of the active compound(s).

Spray compositions may comprise additional substances other than inert diluents: e.g. stabilizing agents (sodium sulfite etc.), isotonic buffer (sodium chloride, sodium citrate, citric acid etc.)

For preparation of such spray compositions, for example, the method described in the U.S. Pat. No. 2,868,691 or 3,095,355 (herein incorporated in their entireties by reference) may be used.

Injections for parenteral administration include sterile aqueous or non-aqueous solutions, suspensions and emulsions. In such compositions, one more of active compound (s) is or are admixed with at least one of inert aqueous diluent(s) (distilled water for injection, physiological salt solution etc.) or inert non-aqueous diluent(s) (propylene glycol, polyethylene glycol, olive oil, ethanol, POLYSOLBATE80 (registered trade mark) etc.).

Injections may comprise additional other than inert diluents: e.g. preserving agents, wetting agents, emulsifying agents, dispersing agents, stabilizing agent (lactose etc.), assisting agents such as assisting agents for dissolving (glutamic acid, aspartic acid etc.).

They may be sterilized for example, by filtration through a bacteria-retaining filter, by incorporation of sterilizing agents in the compositions or by irradiation. They also be manufactured in the form of sterile solid compositions, for example, by freeze-drying, and which can be dissolved in sterile water or some other sterile diluents for injection immediately before use.

Other compositions for parenteral administration include liquids for external use, and endermic liniments (ointment etc.), suppositories and pessaries which comprise one or more of the active compound(s) and may be prepared by known methods.

REFERENCE EXAMPLE AND EXAMPLES

The following Reference examples and examples are intended to illustrate, but not limit, the present invention. In Reference examples and examples, "MP" shows "melting point".

Reference Example 1

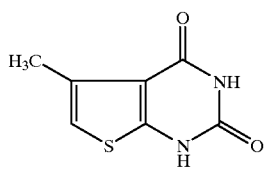

To a solution of 2-amino-4-methylthiophene-3-carboxamide (4.7 g) in 200 mL of tetrahydrofuran was added phosgene (25 mL, 1.93 M solution of toluene) via an addition funnel. The reaction mixture was stirred at room temperature for 2 hours. The reaction mixture was concentrated to a total volume about 10 mL. After cooling, the precipitate was collected by filtration and dried in vacuum to give the title compound (5.3 g) having the following physical data.

MP:291–292° C.;

NMR (200 MHz, DMSO-d6): δ 2.34 (s, 1H), 6.67 (s, 1H), 11.03 (br, 1H), 11.85 (br, 1H).

Reference Example 2

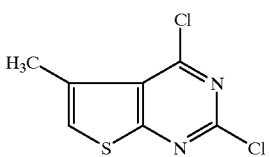

To a warmed suspension of the compound prepared in Reference example 1 (1.82 g) in 7 mL of phosphorous oxychloride was added N,N-dimethylaniline (1.21 g). The reaction mixture was heated to reflux for 1.5 hours. After cooling down to room temperature, the reaction mixture was diluted with 30 mL of dichloromethane and then poured into 100 mL of ice-water. The mixture was extracted with dichloromethane (50 mL×4). The combined extracts were dried over anhydrous sodium sulfate and concentrated to give the title compound (2 g) having the following physical data.

NMR (200 MHz, CDCl₃): δ 2.68 (m, 3H), 7.22 (m, 1H).

Reference Example 3

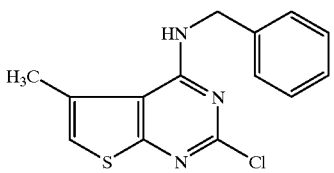

To a solution of the compound prepared in Reference example 2 (1.1 g) in 40 mL of ethanol was added benzylamine (0.54 g). The mixture was heated to reflux overnight. 0.25 g of triethylamine was added after 1 day and 5 mL of 1N aqueous solution of sodium hydroxide was added after 2 days to above reaction mixture. The mixture was stirred for another 15 minutes. The reaction mixture was concentrated and extracted with dichloromethane (20 mL×3), and dried over potassium carbonate. Removal of solvents under reduced pressure, the residue was triturated in ether and filtered to give the title compound (0.56 g) having the following physical data.

NMR (200 MHz, CDCl₃): δ 4.84 (d, 2H), 5.81 (br, 1H), 6.85 (m, 1H), 7.35–7.42 (m, 5H).

Reference Example 4

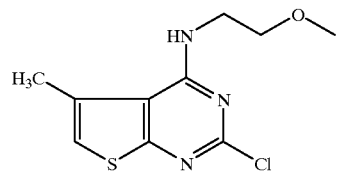

The title compound was obtained by the same procedure as Reference example 3, by using 2-methoxyethylamine instead of benzylamine.

MP: 112–113° C.;

NMR (200 MHz, CDCl₃): δ 2.57 (s, 3H), 3.43 (s, 3H), 3.62 (t, 2H), 3.80 (t, 2H), 6.08 (brs, 1H), 6.82 (s, 1H);

IR (KBr): ν 3410, 2938, 1578, 1548, 1352, 1249, 979, 893, 740 cm⁻¹.

Reference Example 5

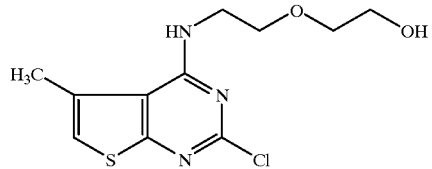

The title compound was obtained by the same procedure as Reference example 3, by using 2-(2-hydroxyethoxy)ethylamine instead of benzylamine.

MP: 101–103° C.;

NMR (200 MHz, DMSO-d6): δ 2.55 (d, 3H), 3.50 (s, 4H), 3.64 (s, 4H), 4.61 (brs, 1H), 7.01 (brs, 1H), 7.19 (d, 1H);

IR (KBr): ν 3435, 2925, 1582, 1458, 1353, 1132, 1023, 852, 763 cm⁻¹.

Reference Example 6

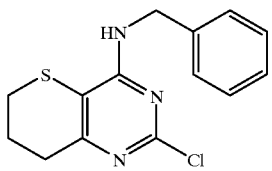

The title compound was obtained by the same procedure as Reference example 3, by using 2,4-dichloro-7,8-dihydro-6H-thiopyrano[3,2-d]pyrimidine (see S. Ohno, et. al., Chem. Pharm. Bull., 34, 4150 (1986)) instead of the compound prepared in Reference Example 2.

TLC: Rf 0.40 (Dichloromethane:Methanol=99:1).

Reference Example 7

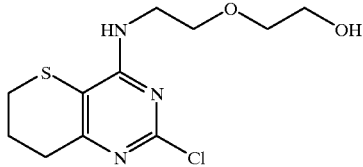

The title compound was obtained by the same procedure as Reference example 5, by using 2,4-dichloro-7,8-dihydro-6H-thiopyrano[3,2-d]pyrimidine instead of the compound prepared in Reference example 2.

TLC: Rf 0.43 (Chloroform:Methanol=19:1).

Reference Example 8

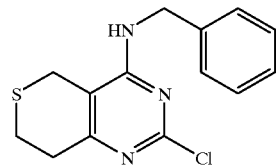

The title compound was obtained by the same procedure as Reference example 3, by using 2,4-dichloro-7,8-dihydro-5H-thiopyrano[3,2-d]pyrimidine (the compound prepared by the same procedure as Chem. Pharm. Bull., 34, 4150 (1986)) instead of the compound prepared in Reference example 2.

TLC: Rf 0.32 (Hexane:Ethyl acetate=3:1);

NMR (200 MHz, CDCl₃): δ 7.45–7.28 (5H, m), 5.00–4.85 (1H, br), 4.69 (2H, d), 3.35 (2H, s), 3.03 (2H, t), 2.86 (2H, t).

Reference Example 9

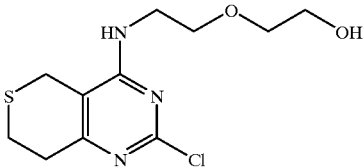

The title compound was obtained by the same procedure as Reference example 5, by using 2,4-dichloro-7,8-dihydro-5H-thiopyrano[3,2-d]pyrimidine instead of the compound prepared in Reference example 2.

TLC: Rf 0.38 (Ethyl acetate);

NMR (200 MHz, CDCl₃): δ 5.45–5.25 (1H, br), 3.82–3.58 (8H, m), 3.39 (2H, s), 3.02 (2H, t), 2.87 (2H, t), 2.10–1.85 (1H, br).

Reference Example 10

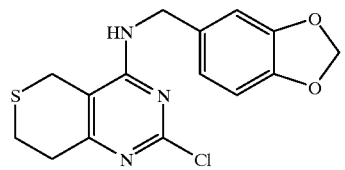

The title compound was obtained by the same procedure as Reference example 8, by using 1,3-benzodioxan-5-methylamine instead of benzylamine.

TLC: Rf 0.19 (Hexane:Ethyl acetate=3:1);

NMR (200 MHz, CDCl₃): δ 6.85–6.75 (3H, m), 5.96 (2H, s), 4.95–4.80 (1H, br), 4.58 (2H, d), 3.34 (2H, s), 3.02 (2H, t), 2.86 (2H, t).

Reference Example 11

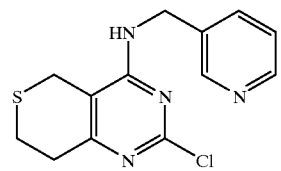

The title compound was obtained by the same procedure as Reference example 8, by using 3-(aminomethyl)pyridine instead of benzylamine.

TLC: Rf 0.59 (Chloroform:Methanol=9:1).

Reference Example 12

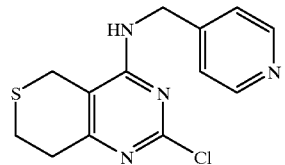

The title compound was obtained by the same procedure as Reference example 8, by using 4-(aminomethyl)pyridine instead of benzylamine.

TLC: Rf 0.60 (Chloroform:Methanol=9:1).

Reference Example 13

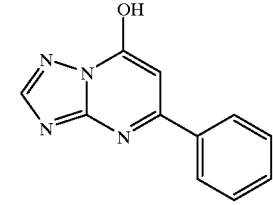

A mixture of 90% ethyl benzoylacetate (22 g) and 3-amino-1,2,4-triazole (8.4 g) in 100 mL of glacial acetic acid was heated at reflux for 18 hours. The mixture was then concentrated to approximately 40 mL and diluted with 400 mL water. The precipitate was collected by filtration. This material was taken up in sodium bicarbonate solution and filtered. The filtrate was acidified with acetic acid and the resulting precipitate was collected by filtration and dried in vacuum to give the title compound (2.3 g) having the following physical data.

MP 286–288 ° C.;

NMR (200 MHz, DMSO-d6): δ 6.37 (s, 1H), 7.52–7.63 (m, 3H), 7.86–7.97 (m, 2H), 8.41 (s, 1H).

Reference Example 14

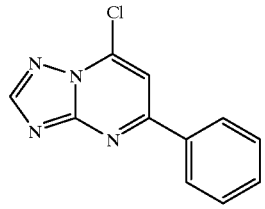

The title compound was obtained by the same procedure as Reference example 2, by using compound prepared in Reference example 13 instead of the compound prepared in Reference example 1.

MP: 163–170° C.;

NMR (200 MHz, CDCl₃): δ 7.57 (m, 3H), 7.70 (s, 1H), 8.20 (m, 2H), 8.57 (s, 1H).

Reference Example 15

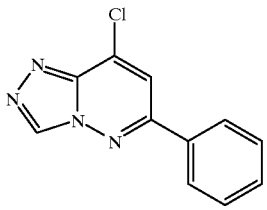

The title compound was obtained by the same procedure as Reference example 13→Reference example 14, by using 1-amine-1,2,4-triazole instead of 3-amino-1,2,4-triazole.

NMR (200 MHz, CDCl₃): δ 7.56 (m, 3H), 7.67 (s, 1H), 7.97 (m, 2H), 9.19 (s, 1H).

Example 1

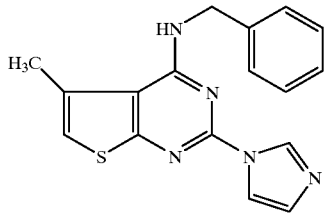

The mixture of the compound prepared in Reference example 3 (0.49 g), imidazole (0.35 g) and phenol (2 g) was heated to reflux for overnight. After cooling down to room temperature, the reaction mixture was diluted with 30 mL of methylene chloride and washed with 1N aqueous solution of sodium hydride (10 mL×3) and dried over potassium carbonate. Removal of the solvents by evaporation, the residue was triturated in ether to give the title compound (0.2 g) having the following physical data.

MP: 185–189° C.;

NMR (200 MHz, CDCl₃): δ 2.55 (s, 3H), 4.83 (d, 2H), 5.95 (br, 1H), 6.77 (s, 1H), 7.11 (s, 1H), 7.26–7.40 (m, 5H), 7.86 (s, 1H), 8.55 (s, 1H).

Example 2

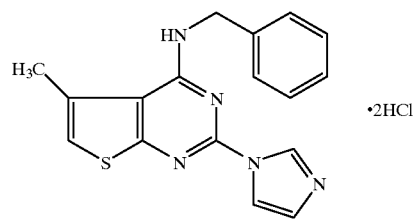

To a suspension of the compound prepared in Example 1 (0.16 g) in 1 mL of methanol was added a saturated methanol solution of hydrochloric acid (0.5 mL) to form a red solution. After stirring at room temperature for 15 minutes, the excess methanol was removed and 10 mL of ether was added to the mixture for triturating. The precipitate was obtained after filtration and dried in vacuum to give the title compound (0.17 g) having the following physical data.

MP: 228–233° C.;

NMR (200 MHz, DMSO-d6): δ 2.69 (s, 3H), 4.91 (d, 2H), 7.25–7.40 (m, 4H), 7.49–7.53 (m, 2H), 7.82 (s, 1H), 8.06 (br, 1H), 8.30 (s, 1H), 9.86 (s, 1H).

Example 2(1)–2(7)

The following compounds were obtained by the same procedure as Example 1→Example 2, by using the corresponding compound prepared by Reference example 4, 5, 6, 7, 8, 9 or 10 and suitable amine, if necessary by using the corresponding methanesulfonic acid instead of hydrochloric acid.

Example 2(1)

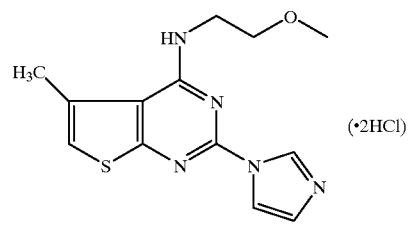

(free base)
MP: 146–151° C.;
NMR (200 MHz, DMSO-d6): δ 2.57 (s, 3H), 3.32 (s, 3H), 3.62 (m, 2H), 3.79 (m, 2H), 7.05 (br, 1H), 7.09 (s, 1H), 7.13 (s, 1H), 7.91 (s, 1H), 8.54 (s, 1H);
IR (KBr): ν 3330, 2925, 1587, 1482, 1423, 1353, 1312, 1099, 1099, 1049, 739, 653 cm⁻¹.
(2HCl salt)
MP: 183–188° C.;
NMR (DMSO-d6): δ 2.61 (s, 3H), 3.32 (s, 3H), 3.62 (t, 2H), 3.85 (q, 2H), 7.29 (s, 1H), 7.33 (brt, 1H), 7.83 (s, 1H), 8.37 (s, 1H), 9.89 (s, 1H);
IR (KBr): ν 3345, 3160, 2800–2500, 1597, 1519, 1403, 1357, 1129, 1050, 832, 768 cm⁻¹.

Example 2(2)

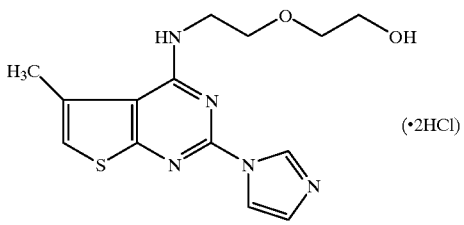

(free base)

MP: 138–140° C.;

NMR (200 MHz, DMSO-d6): δ 2.58 (s, 3H), 3.52 (s, 4H), 3.71 (d, 2H), 3.78 (br, 2H), 4.62 (br, 1H), 7.03 (br, 1H), 7.09 (s, 1H), 7.14 (s, 1H), 7.92 s, 1H), 8.55 (s, 1H);

IR (KBr): ν 3410, 3245, 2920, 1585, 1554, 1475, 1428, 1343, 1312, 1126, 1069, 832 cm$^{-1}$.

(2HCl salt)

MP: 160–163° C.;

NMR (200 MHz, DMSO-d6): δ 2.62 (s, 3H), 3.52 (s, 4H), 3.71 (t, 2H), 3.85 (t, 2H), 7.30 (s, 2H), 7.82 (s, 1H), 8..38 (s, 1H), 9.87 (s, 1H);

IR (KBr): ν 3435, 3155, 2920, 1601, 1523, 1402, 1129, 1065 cm$^{-1}$.

Example 2(3)

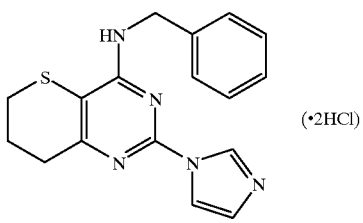

(free base)

TLC: Rf 0.32 (Dichloromethane:Methanol=19:1);

MP: 165–167° C.;

NMR (200 MHz, DMSO-d6): δ 2.12 (m, 2H), 2.76 (m, 2H), 3.12 (m, 2H), 4.65 (d, 2H), 7.01 (s, 1H), 7.20 (t, 1H), 7.30 (t, 2H), 7.39 (d, 2H), 7.59 (m, 1H), 7.72 (s, 1H), 8.33 (s, 1H).

(2HCl salt)

MP: 207.0–217.0° C.;

NMR (200 MHz, DMSO-d6): δ 2.03–2.21 (m, 2H), 2.81 (t, 2H), 3.17 (t, 2H), 4.75 (d, 2H), 7.18–7.41 (m, 5H), 7.77 (s, 1H), 7.85 (m, 1H), 8.17 (s, 1H), 9.73 (s, 1H);

IR (KBr): ν 3468, 3274, 1610, 1516, 1428, 1407, 1380, 1053 cm$^{-1}$.

Example 2(4)

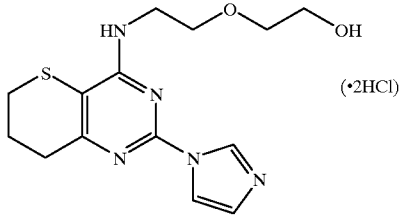

(free base)

TLC: Rf 0.36 (Chloroform:Methanol=19:1);

MASS (EI): 321 (M$^+$).

(2HCl salt)

TLC: Rf 0.36 (Chloroform:Methanol=19:1);

NMR (200 MHz, DMSO-d6): δ 9.83 (1H, s), 8.25 (1H, s), 7.82 (1H, s), 7.15 (1H, t), 3.70 (2H, m), 3.61 (2H, t), 3.50–3.40 (4H, m), 3.20–3.10 (2H, m), 2.80 (2H, t), 2.20–2.05 (2H, m);

IR (KBr): ν 3309, 3104, 3013, 2921, 2392, 1884, 1646, 1594, 1577, 1540, 1511, 1389, 1343, 1113, 1061, 1035, 991, 845, 716, 621 cm$^{-1}$.

Example 2(5)

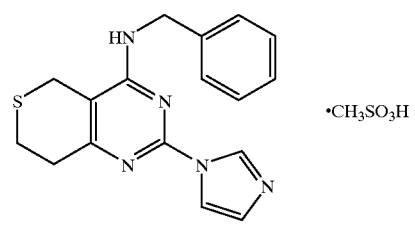

(free base)

TLC: Rf 0.51 (Ethyl acetate);

NMR (200 MHz, DMSO-d6): δ 8.36 (1H, s), 7.95 (1H t), 7.74 (1H, s), 7.44–7.15 (5H, m), 7.01 (1H, s), 4.66 (2H, d), 3.56 (2H, s), 2.90 (4H s).

(CH$_3$SO$_3$H salt)

NMR (200 MHz, DMSO-d6): δ 9.75 (1H, s), 8.33–8.15 (2H, m), 7.79 (1H, s), 7.48–7.18 (5H, m), 4.75 (2H, d), 3.60 (2H, s), 2.94 (4H, s), 2.34 (3H, s).

IR (KBr): ν 3274, 3140, 1617, 1572, 1543, 1524, 1442, 1413, 1391, 1353, 1212, 1158, 1060, 1046, 895, 836, 772, 704, 625, 555, 527 cm$^{-1}$.

Example 2(6)

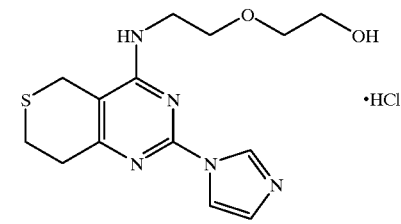

(free base)

TLC: Rf 0.56 (Chloroform:Methanol=8:1);

NMR (200 MHz, DMSO-d6): δ 8.43 (1H, s), 7.81 (1H s), 7.43–7.25 (1H, br), 7.05 (1H, s), 4.68–4.50 (1H, m), 3.75–3.28 (10H, m), 2.90 (4H, s).

(HCl salt)

NMR (200 MHz, DMSO-d6): δ 9.78 (1H, s), 8.26 (1H, s), 7.80 (1H, s), 7.77–7.63 (1H, br), 3.78–3.43 (10H, m), 3.08–2.78 (4H, m);

IR (KBr): ν 3401, 2931, 1613, 1523, 1445, 1391, 1350, 1118, 1059, 881, 772, 623 cm$^{-1}$.

Example 2(7)

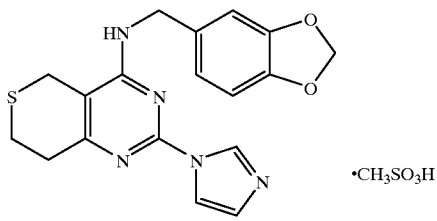

(free base)
TLC: Rf 0.33 (Ethyl acetate).
(CH₃SO₃H salt)
TLC: Rf 0.42 (Ethyl acetate);
NMR (200 MHz, DMSO-d6): δ 9.76 (1H, s), 8.26 (1H, s), 8.23–8.10 (1H, m), 7.80 (1H, s), 7.01 (1H, d), 6.93 (1H, dd), 6.83 (1H, d), 5.95 (2H, s), 4.64 (2H, d), 3.58 (2H, s), 2.94 (4H, s), 2.37 (3H, s);
IR (KBr): ν 3436, 3144, 1616, 1572, 1543, 1524, 1491, 1445, 1415, 1393, 1243, 1210, 1159, 1047, 933, 899, 811, 774, 624, 556 cm⁻¹.

Example 3

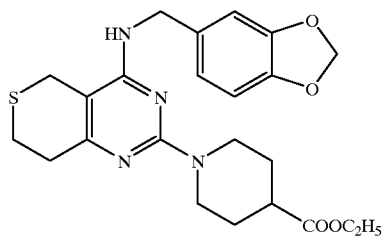

The mixture of the compound prepared in Reference example 10 (0.333 g), isonipecotic acid (0.95 mL) and isopropyl alcohol (6 mL) was heated to reflux for 1 hour. After cooling down to room temperature, the reaction mixture was diluted with chloroform and washed with water and saturated aqueous solution of sodium ammonium and dried over anhydrous sodium sulfate. After removal of the solvents by evaporation, the residue was purified by silica gel column chromatography (chloroform:ethyl acetate= 4:1→2:1) to give the title compound (0.375 g) having the following physical data.
TLC: Rf 0.70 (Chloroform:Ethyl acetate=2:1).

Example 4

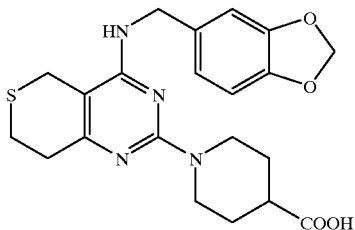

To a solution of the compound prepared in Example 3 (0.375 g) in ethanol (6 mL) was added 1N aqueous solution of sodium hydroxide (0.85 mL) at 0° C. The mixture was stirred at 80° C. for 1.5 hours. The mixture was neutralized by adding 1N aqueous solution of hydrochloric acid and concentrated. The residue was dissolved in methanol and filtered. Removal of the solvents by evaporation to give the title compound (0.259 g) having the following physical data.

TLC: Rf 0.18 (Chloroform:Methanol=6:1);
NMR (200 MHz, DMSO-d6): δ 7.18 (1H, t), 6.90 (1H, s), 6.82–6.75 (2H, m), 5.94 (2H, s), 4.50–4.31 (4H, m), 3.42 (2H, s), 2.95–2.55 (6H, m), 2.42 (1H, brt) 1.82–1.65 (2H, m), 1.46–1.20 (2H, m);
IR (KBr): ν 3411, 2923, 1655, 1625, 1562, 1489, 1444, 1420, 1369, 1239, 1037, 928, 772 cm⁻¹.

Example 4(1) and 4(2)

The following compounds were obtained by the same procedure as Example 3→Example 4, by using the corresponding compound prepared by Reference Example 11 or 12 instead of the compound prepared in Reference example 10.

Example 4(1)

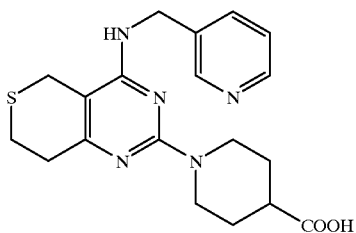

TLC: Rf 0.17 (Chloroform:Methanol=4:1);
NMR (200 MHz, DMSO-d6): δ 8.55 (1H, d), 8.40 (1H, dd), 7.71 (1H, d), 7.30 (1H, dd), 7.26 (1H, brt), 4.51 (2H, d), 4.37 (2H, brd), 3.43 (2H, s), 2.90–2.60 (6H, m), 2.35 (1H, m), 1.80–1.60 (2H, m), 1.42–1.20 (2H, m);
IR (KBr): ν 3399, 2922, 1655, 1626, 1562, 1492, 1420, 1356, 1237, 1032, 714 cm⁻¹.

Example 4(2)

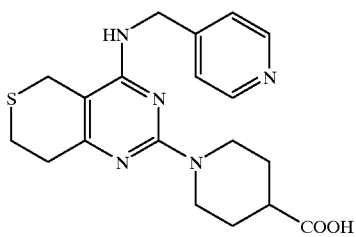

TLC: Rf 0.17 (Chloroform:Methanol=4:1);
NMR (200 MHz, DMSO-d6): δ 8.44 (2H, d), 7.28 (2H, d), 7.28 (1H, brt), 4.50 (2H, d), 4.25 (2H, d), 3.47 (2H, s), 2.85–2.64 (6H, m), 2.30 (1H, m), 1.70–1.58 (2H, m), 1.35–1.15 (2H, m).
IR (KBr): ν 3368, 2922, 1654, 1626, 1562, 1491, 1420, 1360, 1235, 1033, 953, 782, 756 cm⁻¹.

Example 5

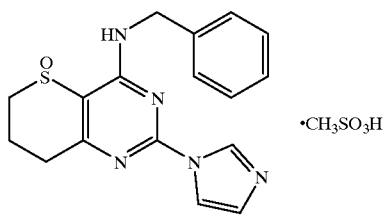

To a solution of the compound prepared in Example 2(3) (0.245 g) in dichloromethane (5 mL) was added a solution of 3-chloroperoxybenzoic acid (0.196 g) in dichloromethane (2 mL) at −10° C. under an atmosphere of argon gas. The mixture was stirred at same temperature for 10 min. The mixture was quenched by addition of a saturated aqueous solution of sodium ammonium, extracted with dichloromethane. The extract was washed with a saturated aqueous solution of sodium hydrocarbonate and saturated aqueous solution of sodium chloride, dried over magnesium sulfate, and concentrated. The residue was purified by silica gel column chromatography (dichloromethane:methanol=49:1) to give the title compound (0.163 g) having the following physical data.
(free base)
TLC: Rf 0.23 (Dichloromethane:Methanol=19:1);
NMR (200 MHz, DMSO-d6): δ 8.80 (1H, t), 8.40 (1H, s), 7.78 (1H, s), 7.42–7.18 (5H, m), 7.02 (1H, s), 4.70 (2H, d), 3.20 (1H, m), 3.10–2.80 (3H, m), 2.40 (1H, m), 2.08 (1H, m).
($CH_3SO_3H$ salt)
TLC: Rf 0.34 (Dichloromethane:Methanol=19:1);
NMR (200 MHz, DMSO-d6): δ 9.73 (1H, s), 9.07 (1H, t), 8.23 (1H, s), 7.77 (1H, s), 7.46–7.20 (5H, m), 4.85 (1H, dd), 4.75 (1H, dd), 3.38–3.20 (1H, m), 3.12–2.95 (1H, m), 2.88–2.80 (2H, m), 2.50–2.30 (1H, m), 2.35 (3H, s), 2.20–2.00 (1H, m);
IR (KBr): ν 3401, 1603, 1515, 1445, 1407, 1349. 1194, 1059, 1032, 884, 785, 705, 623, 563, 537 $cm^{-1}$.

Example 5(1) and 5(2)

The following compounds were obtained by the same procedure as Example 5, by using the corresponding compound prepared by Example 2(5) or 2(6) instead of the compound prepared in Example 2(3).

Example 5(1)

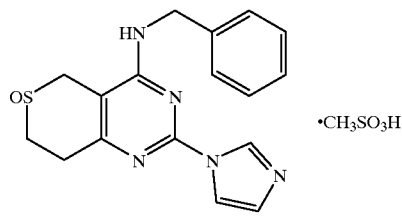

(free base)
TLC: Rf 0.50 (Chloroform:Methanol=7:1);
NMR (200 MHz, DMSO-d6): δ 8.39 (1H, s), 8.07 (1H, t), 7.77 (1H, s), 7.44–7.15 (5H, m), 7.03 (1H, s), 4.66 (2H, d), 3.80 (2H, s), 3.29–2.80 (4H, m).
($CH_3SO_3H$ salt)
NMR (200 MHz, DMSO-d6): δ 9.82 (1H, s), 8.37 (1H, t), 8.27 (1H, s), 7.82 (1H, s), 7.48–7.18 (5H, m), 4.76 (2H, d), 3.84 (2H, s), 3.35–2.85 (4H, s), 2.35 (3H, s).

IR (KBr): ν 3435, 3257, 3167, 1612, 1573, 1542, 1522, 1441, 1411, 1392, 1350, 1197, 1060, 1043, 893, 829, 785, 774, 751, 705, 623, 563, 537, 506 $cm^{-1}$.

Example 5(2)

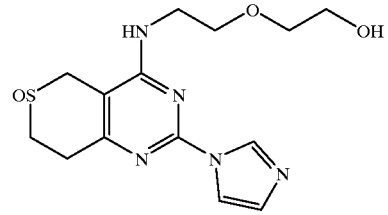

TLC: Rf 0.28 (Chloroform:Methanol=8:1);
NMR (200 MHz, DMSO-d6): δ 8.46 (1H, s), 7.83 (1H, s), 7.58–7.38 (1H, br), 7.06 (1H, s), 4.70–4.53 (1H, br), 3.90–2.80 (14H, m);
IR (KBr): ν 3401, 2930, 1603, 1536, 1479, 1450, 1342, 1201, 1120, 1057, 1026, 834, 752, 656, 613 $cm^{-1}$.

Example 6

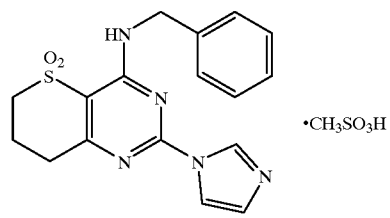

To a solution of the compound prepared in Example 2(3) (0.152 g) in dichloromethane (3 mL) was added a solution of 70% 3-chloroperoxybenzoic acid (0.238 g) in dichloromethane (3 mL) at 0° C. under an atmosphere of argon gas. The mixture was stirred at same temperature for 2 hours and at room temperature for 3 hours. The mixture was quenched by addition of a saturated aqueous solution of sodium ammonium, extracted with dichloromethane. The extract was washed with a saturated aqueous solution of sodium hydrocarbonate and saturated aqueous solution of sodium chloride, dried over magnesium sulfate, and concentrated. The residue was purified by silica gel column chromatography (dichloromethane:methanol=19:1) to give the title compound (0.168 g) having the following physical data.
(free base)
TLC: Rf 0.59 (Dichloromethane:Methanol=19:1);
NMR (200 MHz, DMSO-d6): δ0 8.40 (1H, s), 8.10 (1H, t), 7.78 (1H, s), 7.40–7.20 (5H, m), 7.05 (1H, s), 4.78 (2H, d), 3.60 (2H, m), 2.90 (2H, m), 2.30 (2H, m).
($CH_3SO_3H$ salt)
TLC: Rf 0.43 (Dichloromethane:Methanol=19:1).
NMR (200 MHz, DMSO-d6): δ 9.68 (1H, s), 8.28 (1H, t), 8.20 (1H, s), 7.75 (1H, s), 7.45–7.20 (5H, m), 4.86 (2H, d), 3.71–3.65 (2H, m), 3.02–2.92 (2H, m), 2.40–2.22 (2H, m), 2.36 (3H, s);
IR (KBr): ν 3436, 1611, 1524, 1450, 1412, 1274, 1210, 1051, 761, 704 $cm^{-1}$.

Example 6(1) and 6(2)

The following compounds were obtained by the same procedure as Example 6, by using the corresponding compound prepared by Example 2(5) or 2(6) instead of the compound prepared in Example 2(3).

Example 6(1)

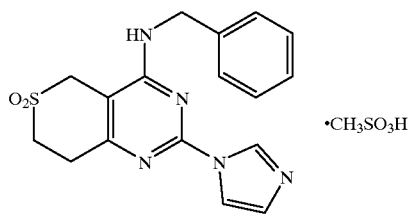

•CH₃SO₃H (free base)
TLC: Rf 0.62 (Chloroform:Methanol=7:1);
NMR (200 MHz, DMSO-d6): δ 8.40 (1H, s), 8.15–8.03 (1H, m), 7.77 (1H, s), 7.45–7.15 (5H, m), 7.04 (1H, s) 4.66 (2H, d), 3.54 (2H, t), 3.20 (2H, t).
(CH₃SO₃H salt)
NMR (200 MHz, DMSO-d6): δ 9.80 (1H, s), 8.43–8.23 (2H, m), 7.81 (1H, s), 7.48–7.18 (5H, m), 4.76 (2H, d), 4.27 (2H, s), 3.59 (2H, t), 3.26 (2H, t),
IR (KBr): ν 3436, 3259, 3141, 1614, 1543, 1524, 1450, 1397, 1353, 1324, 1289, 1209, 1131, 1114, 1060, 902, 776, 702, 626, 555, 445 cm⁻¹.

Example 6(2)

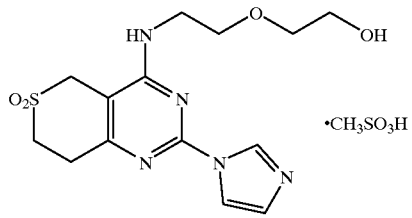

•CH₃SO₃H (free base)
TLC: Rf 0.44 (Chloroform:Methanol=8:1);
NMR (200 MHz, DMSO-d6): δ 8.47 (1H, s), 7.83 (1H, s), 7.55–7.43 (1H, m), 7.07 (1H, s), 4.63–4.55 (1H, m), 4.15 (2H, s), 3.70–3.13 (12H, m).
(CH₃SO₃H salt)
NMR (200 MHz, DMSO-d6): δ 9.79 (1H, s), 8.30–8.25 (1H, m), 7.85–7.73 (2H, m), 4.21 (2H, s), 3.25 (2H, t), 3.78–3.43 (10H , m), 2.33 (3H, s);
IR (KBr): ν 3410, 3275, 3144, 2969, 1615, 1523, 1449, 1392, 1349, 1323, 1287, 1209, 1193, 1118, 1053, 866, 786, 619, 563, 444 cm⁻¹.

Example 7

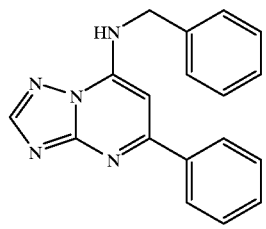

A mixture of the compound prepared in Reference example 14 (0.48 g) and benzylamine (0.42 g) in 30 mL of ethanol was heated at reflux for 18 hours. The mixture was then concentrated. The concentrate was treated with potassium carbonate solution and extracted with methylene chloride. The organic extract was dried over anhydrous magnesium sulfate and concentrated. The concentrate was triturated in ether and collected to give the title compound (0.5 g) having the following physical data.

MP: 151° C.;

NMR (200 MHz, CDCl₃): δ 4.72 (d, 2H), 6.59 (s, 1H), 7.30–7.52 (m, 8H), 8.02–8.12 (m, 2H), 8.35 (s, 1H).

Example 7(1) and 7(2)

The following compounds were obtained by the same procedure as Example 7, by using the corresponding amine instead of benzylamine.

Example 7(1)

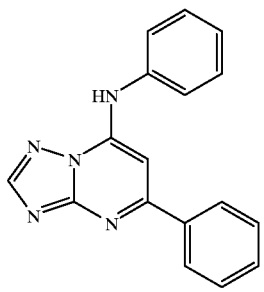

MP: 217–220° C.;

NMR (200 MHz, CDCl₃): δ 6.97 (s, 1H), 7.32–7.60 (m, 8H), 7.90 (s, 1H), 8.12–8.15 (m, 2H), 8.44 (s, 1H).

Example 7(2)

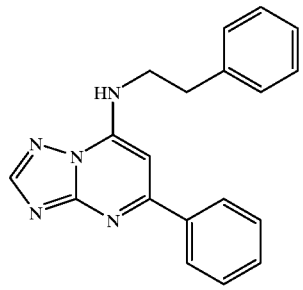

MP: 163–165° C.;

NMR (200 MHz, CDCl₃): δ 3.10 (t, 2H), 3.77 (t, 2H), 6.26 (t, 1H), 6.52 (s, 1H), 7.23–7.43 (m, 5H), 7.49 (m, 3H), 8.10 (m, 2H), 8.32 (s,1H).

Example 8

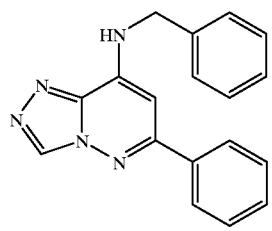

The following compounds were obtained by the same procedure as Example 7, by using the corresponding compound prepared in Reference example 15 instead of the compound prepared in Reference example 14.

MP: 276–278° C.;

NMR (200 MHz, CDCl$_3$): δ 4.75 (d, 2H), 6.32 (s, 1H), 7.25–7.57 (m, 8H), 7.82 (m, 2H), 8.99 (s, 1H).

Formulation Example 1

The following components were admixed in conventional method and punched out to obtain 100 tablets each containing 50 mg of active ingredient.

| | |
|---|---|
| 4-benzylamino-2-(1-imidazolyl)-5-methylthieno[2,3-d]pyrimidine dihydrochloric acid (Example 2) | 5.0 g |
| cellulose calcium glycolate (disintegrating agent) | 0.2 g |
| magnesium stearate (lubricating agent) | 0.1 g |
| micro crystalline cellulose | 4.7 g |

What is claimed is:

1. Heterocyclic compounds of the formula (1):

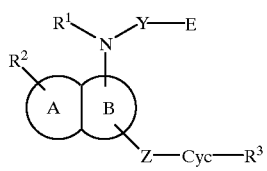

wherein ring

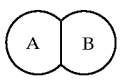

is a

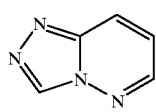

wherein

Y is single bond or C1–6 alkylene;

Z is single bond, or C1–2 alkylene or vinylene;

E is
  (i) 4–15 membered, unsaturated, partially saturated or fully saturated, mono or bicyclic hetero ring containing as hetero atoms, one or two nitrogen atoms, one or two oxygen atoms or one sulfur atom,
  (ii) 4–15 membered, unsaturated or partially saturated, mono or bicyclic carbocyclic ring, or
  (iii) —OR$^4$ (in which R$^4$ is hydrogen atom, C1–4 alkyl or C1–4 alkyl substituted by a hydroxy group);

Cyc is 5–7 membered, unsaturated, partially saturated or fully saturated, monocyclic hetero ring containing as hetero atoms, one or two nitrogen atoms or 5–7 membered, unsaturated or partially saturated, monocyclic carbocyclic ring;

R$^1$ is hydrogen atom or C1–4 alkyl;

R$^2$ is hydrogen atom, C1–4 alkyl, C1–4 alkoxy or halogen atom;

R$^3$ is hydrogen atom, C1–4 alkyl, C1–4 alkoxy or —COOR$^5$ (in which R$^5$ is hydrogen atom or C1–4 alkyl);

with the proviso that
  (1) a Cyc ring should not bond to Z through a nitrogen atom in the Cyc ring when Z is vinylene and that
  (2) Y is not a single bond, when E is —OR$^4$;

or pharmaceutically acceptable acid addition salts thereof, pharmaceutically acceptable salts thereof, or hydrates thereof.

2. A compound according to claim 1, wherein Cyc is 7-membered, unsaturated, partially saturated or fully saturated, monocyclic hetero ring containing as hetero atoms, one or two nitrogen atoms.

3. A compound according to claim 1, wherein Cyc is 6-membered, unsaturated, partially saturated or fully saturated, monocyclic hetero ring containing as hetero atoms, one or two nitrogen atoms.

4. A compound according to claim 1, wherein Cyc is 5-membered, unsaturated, partially saturated or fully saturated, monocyclic hetero ring containing as hetero atoms, one or two nitrogen atoms.

5. A compound according to claim 1, wherein Cyc is 5–7 membered, unsaturated or partially saturated, monocyclic carbocyclic ring.

6. A compound according to claim 1, wherein E is —OR$^4$.

7. A compound according to claim 1, wherein E is 4–15 membered, unsaturated, partially saturated or fully saturated, mono or bicyclic hetero ring containing as hetero atoms, one or two nitrogen atoms, one or two oxygen atoms or one sulfur atom.

8. A compound according to claim 1, wherein E is 4–15 membered, unsaturated or partially saturated, mono or bicyclic carbocyclic ring.

9. A compound according to claim 1, which is

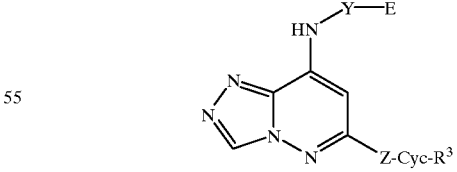

wherein
Y is methylene, E is phenyl, Z is single bond, Cyc is phenyl and R$^3$ is hydrogen atom;

or pharmaceutically acceptable acid addition salts thereof, pharmaceutically acceptable salts thereof, or hydrates thereof.

10. A pharmaceutical composition for the treatment of mammals, which comprises, as active ingredient, an effective amount of a compound of the formula (1) as claimed in claim 1, pharmaceutically acceptable acid addition salts thereof, pharmaceutically acceptable salts thereof, or hydrates thereof; and a pharmaceutically acceptable carrier.

11. The pharmaceutical composition according to claim 10, wherein the mammal is a human.

* * * * *